(12) United States Patent
Ohta et al.

(10) Patent No.: US 7,787,594 B2
(45) Date of Patent: Aug. 31, 2010

(54) RADIATION IMAGE CAPTURING METHOD, RADIATION IMAGE CAPTURING SYSTEM AND RADIATION INFORMATION SYSTEM FOR CARRYING OUT RADIATION IMAGE CAPTURING METHOD

(75) Inventors: Yasunori Ohta, Kanagawa (JP); Eiichi Kito, Kanagawa (JP); Tsuyoshi Tanabe, Kanagawa (JP); Takuya Yoshimi, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 87 days.

(21) Appl. No.: 12/219,403

(22) Filed: Jul. 22, 2008

(65) Prior Publication Data

US 2009/0028298 A1  Jan. 29, 2009

(30) Foreign Application Priority Data

| Jul. 26, 2007 | (JP) | ............................. 2007-194842 |
| Jul. 26, 2007 | (JP) | ............................. 2007-194843 |
| Jun. 3, 2008 | (JP) | ............................. 2008-145446 |
| Jun. 3, 2008 | (JP) | ............................. 2008-145849 |

(51) Int. Cl.
*H05G 1/30* (2006.01)

(52) U.S. Cl. ...................................... 378/114; 378/207

(58) Field of Classification Search ......... 378/115–116, 378/189–190, 102, 207, 204, 210, 98.8
See application file for complete search history.

(56) References Cited

U.S. PATENT DOCUMENTS

| 6,268,614 B1 | 7/2001 | Imai |
| 2007/0116180 A1* | 5/2007 | Omernick et al. ............ 378/116 |
| 2008/0292062 A1* | 11/2008 | Marar ........................ 378/207 |

FOREIGN PATENT DOCUMENTS

| JP | 07-140255 | 6/1995 |
| JP | 2000-105297 | 4/2000 |
| JP | 2004-141473 | 5/2004 |
| JP | 2006-198043 | 8/2006 |

* cited by examiner

*Primary Examiner*—Hoon Song
(74) *Attorney, Agent, or Firm*—Jean C. Edwards, Esq.; Akerman Senterfitt

(57) ABSTRACT

A radiation image capturing method, a radiation image capturing system, and a radiation information system are provided. In the present invention, a console checks a cassette ID (specified cassette ID) sent from an RIS server as the cassette ID of a radiation detecting cassette that is planned to be used to capture a radiation image, and a cassette ID (actual cassette ID) that is read by the console from a radiation detecting cassette which is placed in an operating room or an image capturing room and which is to be actually used to capture a radiation image, with each other. Based on the result of the cassette ID check, the console determines whether to permit a radiation image to be captured or not.

18 Claims, 17 Drawing Sheets

FIG. 13
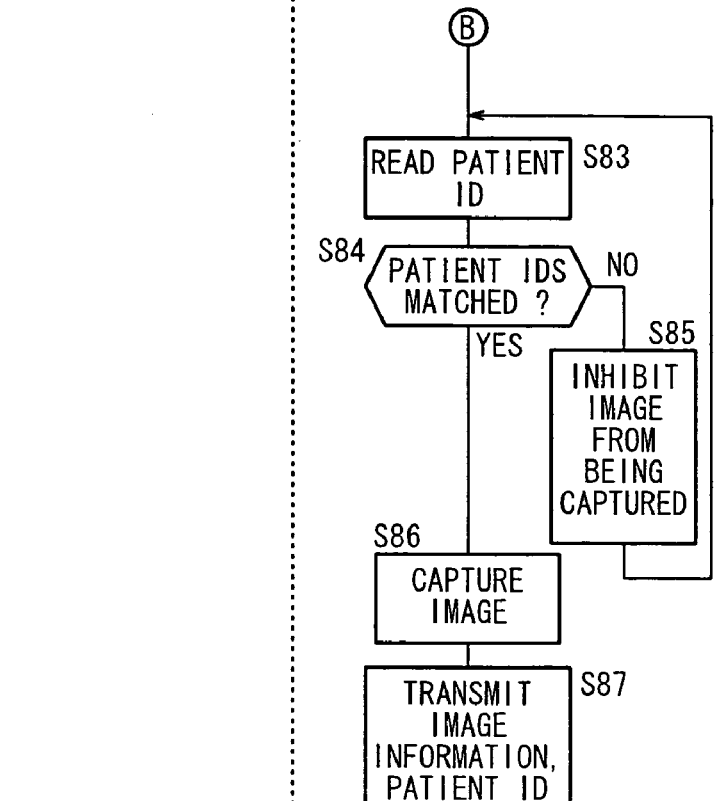
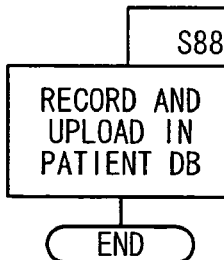

RADIATION IMAGE CAPTURING METHOD, RADIATION IMAGE CAPTURING SYSTEM AND RADIATION INFORMATION SYSTEM FOR CARRYING OUT RADIATION IMAGE CAPTURING METHOD

CROSS-REFERENCE TO RELATED APPLICATIONS

The present application claims priority from Japanese Patent Application Nos. 2007-194842, filed Jul. 26, 2007, 2007-194843, filed Jul. 26, 2007, 2008-145446, filed Jun. 3, 2008, and 2008-145849, filed Jun. 3, 2008 the contents of all of which are herein incorporated by reference in their entirety.

BACKGROUND OF THE INVENTION

1. Field of the Invention

The present invention relates to a radiation image capturing method employing a radiation conversion panel for detecting a radiation that has passed through a subject and converting the detected radiation into radiation image information, and a radiation image capturing system and a radiation information system for carrying out such a radiation image capturing method, and more particularly to a radiation image capturing method for identifying a radiation conversion panel, and a radiation image capturing system and a radiation information system for carrying out such a radiation image capturing method.

2. Description of the Related Art

In the medical field, there have widely been used radiation image capturing apparatus which apply a radiation to a subject and guide the radiation that has passed through the subject to a radiation conversion panel, which captures a radiation image from the radiation. Known forms of the radiation conversion panel include a conventional radiation film for recording a radiation image by way of exposure, and a stimulable phosphor panel for storing a radiation energy representing a radiation image in a phosphor and reproducing the radiation image as stimulated light by applying stimulating light to the phosphor. The radiation film with the recorded radiation image is supplied to a developing device to develop the radiation image, or the stimulable phosphor panel is supplied to a reading device to read the radiation image as a visible image.

In the operating room or the like, it is necessary to read and display a recorded radiation image immediately from a radiation conversion panel after the radiation image is captured for the purpose of quickly and appropriately treating the patient. As a radiation conversion panel which meets such a requirement, there has been developed a radiation detector having solid-state detectors for converting a radiation directly into an electric signal or converting a radiation into visible light with a scintillator and then converting the visible light into an electric signal to read a detected radiation image. The radiation conversion panel is separate from a console as a controller and a radiation source because the radiation conversion panel is used to capture radiation images of various areas of patients (see Japanese Laid-Open Patent Publication No. 2004-141473). Radiation conversion panels that are capable of wireless communications have been introduced into the art because they are highly convenient to use.

Radiation image capturing systems which employ radiation conversion panels are required to prevent the radiation conversion panels from being mixed up or mistaken in use.

Japanese Laid-Open Patent Publication No. 2004-141473 discloses an X-ray image capturing system including a removable adapter having identification information of a wireless cassette recorded therein and mounted in an adapter mounting slot in the wireless cassette. When the wireless cassette is in use, the removable adapter is removed from the adapter mounting slot in the wireless cassette, and inserted into an adapter mounting slot in an X-ray generator, which detects the identification information of the cassette from the adapter, so that the wireless cassette and the X-ray generator can be combined with each other (the abstract of Japanese Laid-Open Patent Publication No. 2004-141473).

However, since the adapter that is holding the identification information of the cassette is removable from the cassette, if the adapter is missing, the identification information of the cassette is lost. According to Japanese Laid-Open Patent Publication No. 2004-141473, the identification information recorded in the adapter and the identification information recorded in the cassette itself are checked against each other. The X-ray image capturing system operates normally insofar as the adapter and the cassette are in proper combination. If wireless cassettes for use with the X-ray image capturing system are mixed up and the wrong wireless cassette is used with the X-ray image capturing system, the disclosed X-ray image capturing system is unable to detect such a confusion.

Japanese Laid-Open Patent Publication No. 2006-198043 discloses a system for saving image data captured by a radiation image capturing apparatus according to an examination instruction, in combination with patient information (the abstract, etc. of Japanese Laid-Open Patent Publication No. 2006-198043).

According to the system disclosed in Japanese Laid-Open Patent Publication No. 2006-198043, though not explicitly stated, the operator (radiological technician) judges whether the combination of the patient information and the image data is proper or not. Therefore, there is a possibility that the patient information and the image data may be improperly combined with each other. Specifically, though the operator is required to select a film according to the examination instruction, the operator may possibly use a different film due to a clerical oversight. It is customary for the operator to confirm the proper combination of the patient information and the image data by checking the name of the subject (patient) with the subject. If the subject gives a wrong answer to the operator, then the operator may possibly mistake the subject for someone else.

SUMMARY OF THE INVENTION

It is an object of the present invention to provide a radiation image capturing method which is capable of reliably detecting identification information of a radiation conversion panel to prevent the radiation conversion panel from being mistaken, and a radiation image capturing system and a radiation information system for carrying out such a radiation image capturing method.

Another object of the present invention is to provide a radiation image capturing method which is capable of preventing radiation conversion panels and patients from being mixed up or mistaken, and a radiation image capturing system and a radiation information system for carrying out such a radiation image capturing method.

According to the present invention, there is provided a method of capturing a radiation image with a radiation image capturing system including a conversion panel for detecting a radiation that has passed through a subject and converting the detected radiation into radiation image information, a conversion panel identification information reading unit for reading conversion panel identification information which is stored in the conversion panel to identify the conversion panel, from the conversion panel, and an identifying unit for identifying the conversion panel with the conversion panel identification information, the method comprising the image capturing permission determining step of checking, with the identifying unit, specified conversion panel identification information, which is the conversion panel identification information of a conversion panel that is planned to be used to capture a radiation image, and actual conversion panel identification information, which is the conversion panel identification information of a conversion panel that is to be actually used to capture a radiation image, against each other, and determining, with the identifying unit, whether the radiation image is permitted to be captured or not, based on the result of checking the specified and actual conversion panel identification information.

Since the conversion panel identification information is read from the conversion panel itself which is actually used to capture the radiation image, the conversion panel identification information is reliably detected.

Furthermore, the specified conversion panel identification information, which is the conversion panel identification information of a conversion panel that is planned to be used to capture a radiation image, and the actual conversion panel identification information, which is the conversion panel identification information of a conversion panel that is to be actually used to capture a radiation image, are checked against each other by the identifying unit. The conversion panel is thus reliably prevented from being mistaken.

The method should preferably further comprise the steps of emitting a request signal for requesting the actual conversion panel identification information, from the conversion panel identification information reading unit into a predetermined range for a predetermined time period until communications with the conversion panel that is to be actually used are established, and sending the actual conversion panel identification information from the conversion panel that is to be actually used, to the conversion panel identification information reading unit when the conversion panel that is to be actually used receives the request signal.

The actual conversion panel identification information can thus be read by way of wireless communications, and hence can be read with ease.

The method should preferably further comprise the step of inhibiting a radiation source from applying the radiation if the identifying unit judges that the radiation image is not permitted to be captured in the image capturing permission determining step.

Consequently, if the identifying unit judges that the radiation image is not permitted to be captured, the radiation is automatically inhibited from being applied for higher safety.

The radiation image capturing system further includes a patient identification information storing unit for storing patient identification information for identifying individual patients, the patient identification information storing unit being carried by the individual patients, and a patient identification information reading unit for reading the patient identification information from the patient identification information storing unit. The method should preferably further comprise the second image capturing permission determining step of checking, with the identifying unit, specified patient identification information, which is the patient identification information of a patient that is planned to be imaged, and actual patient identification information, which is the patient identification information of a patient that is to be actually imaged and which is read from the patient identification information storing unit by the patient identification information reading unit, against each other, and determining, with the identifying unit, whether the radiation image is permitted to be captured or not, based on the result of checking the specified and actual patient identification information.

As the specified patient identification information and the actual patient identification information are checked against each other by the identifying unit, the patient is reliably prevented from being mistaken.

The radiation image capturing system further includes an image capturing request input terminal for inputting an image capturing request for the radiation image in association with the patient identification information, and a server having a conversion panel attribute information database for storing the conversion panel identification information and specification information of the conversion panel in association with each other as conversion panel attribute information. The method should preferably further comprise the steps of receiving the image capturing request in association with the patient identification information at the image capturing request input terminal, sending details of the image capturing request and the patient identification information from the image capturing request input terminal to the server, selecting, with the server, a conversion panel corresponding to the details of the image capturing request using the conversion panel attribute information database, and sending conversion panel identification information of the selected conversion panel, together with the details of the image capturing request and the patient identification information of the patient associated with the image capturing request, from the server to the identifying unit.

The radiation image capturing system is easy and efficient to use because it is managed as part of a greater system which includes the image capturing request input terminals and the server. Since the conversion panel identification information and the patient identification information are managed altogether by the server, the radiation image capturing system can also be used easily and efficiently.

According to the present invention, there is also provided a radiation image capturing system for carrying out the above method, and there is also provided a radiation information system comprising a radiation image capturing system, a server, and an image capturing request input terminal for carrying out the above method.

According to the present invention, there is further provided a method of capturing a radiation image with a radiation image capturing system including a conversion panel for detecting a radiation that has passed through a subject and converting the detected radiation into radiation image information, a conversion panel identification information reading unit for reading conversion panel identification information which is stored in the conversion panel to identify the conversion panel, from the conversion panel, and an identifying unit for identifying the conversion panel with the conversion panel identification information, the method comprising the specification matching determining step of comparing, with the identifying unit, requisite specifications, which are specifications of a conversion panel that is planned to be used to capture a radiation image, and actual specifications, which are specifications of a conversion panel that is to be actually used to capture a radiation image and from which the conversion panel identification information is read by the conversion panel identification information reading unit, with each other, and determining whether the actual specifications match the requisite specifications or not, and the image capturing permission determining step of determining, with the identifying unit, whether the radiation image is permitted to be captured or not, based on the result in the specification matching determining step.

According to the present invention, the actual specifications and requisite specifications of cassettes are compared with each other, and whether to permit a radiation image to be captured or not is determined based on the result of the specifications comparison. The conversion panel is thus reliably prevented from being mistaken.

The specifications of the conversion panel may represent a sensitivity or size of the conversion panel.

The method should preferably further comprise the step of inhibiting a radiation source from applying the radiation if the identifying unit judges that the radiation image is not permitted to be captured in the image capturing permission determining step. Consequently, if the identifying unit judges that the radiation image is not permitted to be captured, the radiation is automatically inhibited from being applied for higher safety.

The method should preferably further comprise the step of permitting a radiation source to apply the radiation if the identifying unit judges that the actual specifications are the same as or better than the requisite specifications in the image capturing permission determining step. If the actual specifications are not the same as but better than the requisite specifications, then the radiation is permitted to be applied. Consequently, even if actual cassettes are available in few types, radiation images can be captured in those cassettes while meeting the requisite specifications.

The method should preferably further comprise the step of bringing the conversion panel that is to be actually used, from a power saving mode to a normal mode when the conversion panel identification information reading unit requests the conversion panel to send the conversion panel identification information therefrom. The power consumption of the conversion panel is reduced when no radiation image is captured in the conversion panel.

The radiation image capturing system further includes a patient identification information storing unit for storing patient identification information for identifying individual patients, the patient identification information storing unit being carried by the individual patients, and a patient identification information reading unit for reading the patient identification information from the patient identification information storing unit. The method should preferably further comprise the second image capturing permission determining step of checking, with the identifying unit, specified patient identification information, which is the patient identification information of a patient that is planned to be imaged, and actual patient identification information, which is the patient identification information of a patient that is to be actually imaged and which is read from the patient identification information storing unit by the patient identification information reading unit, against each other, and determining, with the identifying unit, whether the radiation image is permitted to be captured or not, based on the result of checking the specified and actual patient identification information. Inasmuch as the specified patient identification information and the actual patient identification information are checked against each other by the identifying unit, the patient is reliably prevented from being mistaken.

A plurality of image capturing requests are sent to the radiation image capturing system, and the method should preferably further comprise the step of, if the specified patient identification information and the actual patient identification information do not match each other with respect to a first one of the image capturing requests, carrying out the second image capturing permission determining step again with respect to the remaining ones of the image capturing requests. Therefore, even if an error occurs in the sequence of radiation images to be captured, radiation images can quickly be captured by ignoring the sequence of radiation images to be captured.

The patient identification information reading unit and the conversion panel identification information reading unit are disposed near an exit of a place in which the radiation image is captured. The method should preferably further comprise the steps of reading, with the patient identification information reading unit, the patient identification information of a patient whose radiation image has been captured, and sending the read patient identification information to the identifying unit, reading, with the conversion panel identification information reading unit, the conversion panel identification information of a conversion panel which has captured a radiation image, and sending the read conversion panel identification information to the identifying unit, and temporarily inhibiting, with the identifying unit, a next radiation image from being captured until the patient identification information of the patient whose radiation image has been captured and the conversion panel identification information of the conversion panel which has captured the radiation image are received by the identifying unit.

With the above arrangement, a next radiation image cannot be captured until the patient whose radiation image has been captured leaves the place in which the radiation image is captured and the conversion panel which has captured the radiation image are taken out of the place in which the radiation image is captured. Accordingly, patients and cassettes which are close in the image capturing sequence are prevented from being mixed up or mistaken.

According to the present invention, there is further provided a radiation image capturing system for carrying out the above method, and there is further provided a radiation information system comprising a radiation image capturing system, a server, and an image capturing request input terminal for carrying out the above method.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 13 is a flowchart of another part, following the part shown in FIG. 12, of the operation sequence according to the first modification;

DESCRIPTION OF THE PREFERRED EMBODIMENTS

Figure 1:
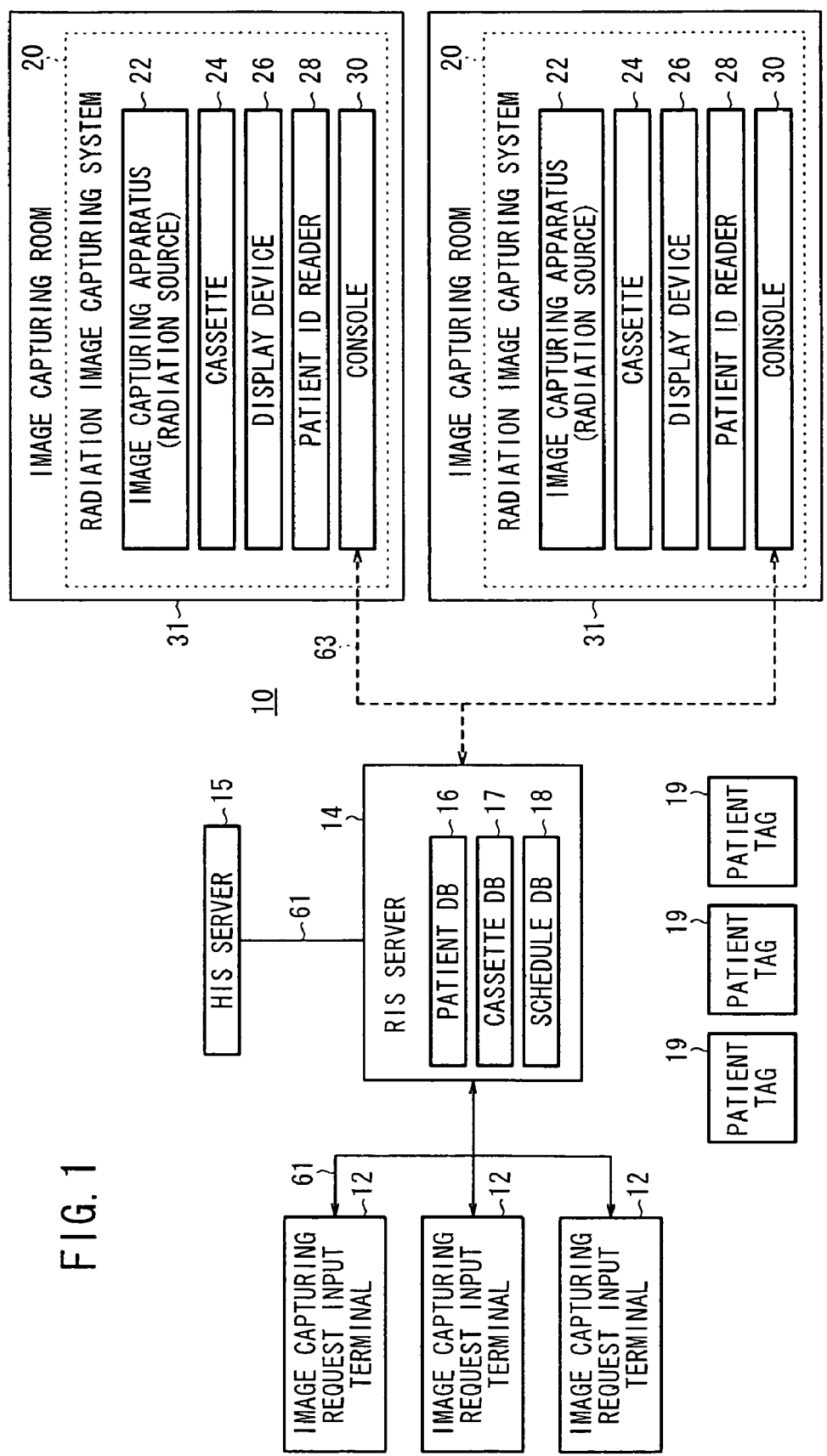
FIG. 1 is a block diagram of a radiation information system according to a first embodiment of the present invention.

Like or corresponding parts are denoted by like or corresponding reference characters throughout views.

A. 1st Embodiment

1. System Setup (1) Overall Configuration:

FIG. 1 is a block diagram showing the components of a radiation information system 10 (hereinafter also referred to as "RIS 10" (RIS: Radiology Information System)) according to a first embodiment of the present invention.

The RIS 10 is a system for managing information about medical care bookings, diagnostic records, etc. in the radiological department of a hospital, and serves as part of a hospital information system (HIS).

The RIS 10 comprises a plurality of image capturing request input terminals 12 (hereinafter also referred to as "input terminals 12"), an RIS server 14, a plurality of radiation image capturing systems 20 (hereinafter also referred to as "image capturing systems 20"), and a plurality of patient tags 19 storing patient identification information (hereinafter also referred to as "patient ID") for identifying individual patients 71 (see FIG. 2) and carried by the respective patients 71. The patient tags 19 are so-called wireless tags, and have the stored patient IDs readable by way of wireless communications.

The RIS server 14 serves to manage the RIS 10 in its entirety, and is linked to the input terminals 12 and the image capturing systems 20 for mutual communications by cables 61 or a wireless LAN 63. The RIS server 14 is connected to an HIS server 15 which manages the HIS in its entirety. The patient tags 19 are capable of performing wireless communications with patient ID readers 28 of the respective image capturing systems 20.

(2) Image Capturing Request Input Terminals 12:

The image capturing request input terminals 12 are used by surgeons 75 (FIG. 2) and a radiological technician to enter and view diagnostic information and facility bookings. Image capturing requests (image capturing bookings) are also entered using the image capturing request input terminals 12. The image capturing request input terminals 12, each comprising a personal computer with a display device, are connected to the RIS server 14 and the HIS server 15 by LAN for communications therewith.

(3) RIS Server 14:

The RIS server 14 serves to receive image capturing requests from the image capturing request input terminals 12 and manage a schedule for capturing radiation images with the radiation image capturing systems 20. The RIS server 14 comprises a patient database 16 (hereinafter also referred to as "patient DB 16"), a cassette database 17 (hereinafter also referred to as "cassette DB 17"), and a schedule database 18 (hereinafter also referred to as "schedule DB 18").

The patient DB 16 contains information about the patient 71, including attribute information of the patient 71 (name, gender, date of birth, age, blood type, patient ID, etc.), clinical history, diagnostic history, radiation images captured in the past.

The cassette DB 17 contains information about a radiation detecting cassette 24 (hereinafter also referred to as "cassette 24") of each of the image capturing systems 20, including identification number (hereinafter also referred to as "cassette ID"), type, size, sensitivity, area to be imaged for which the cassette 24 can be used (details of image capturing requests that can be handled by the cassette 24), date of first use, number of times that the cassette 24 has been used, etc.

The schedule DB 18 serves to manage the schedule for using each of the radiation image capturing systems 20.

(4) Radiation Image Capturing System 20:

(a) Outline of Image Capturing System 20:

Each of the image capturing systems 20 is operated by the radiological technician to capture a radiation image based on instructions from the RIS server 14. Each of the image capturing systems 20 comprises an image capturing apparatus 22 for irradiating the patient 71 (FIG. 2) with a radiation X at a dose according to image capturing conditions, a radiation detecting cassette 24 housing therein a radiation detector, to be described later, for detecting the radiation X that has passed through the patient 71 and converting the detected radiation X into radiation image information, a display device 26 for displaying a radiation image based on the radiation X that is detected by the radiation detector, a patient ID reader 28 for reading the patient ID from the patient tag 19 of the patient 71 by way of wireless communications, and a console 30 for controlling the image capturing apparatus 22, the cassette 24, the display device 26, and the patient ID reader 28. The image capturing apparatus 22, the cassette 24, the display device 26, and the patient ID reader 28 send signals to and receive signals from the console 30 by way of wireless communications.

Figure 2:
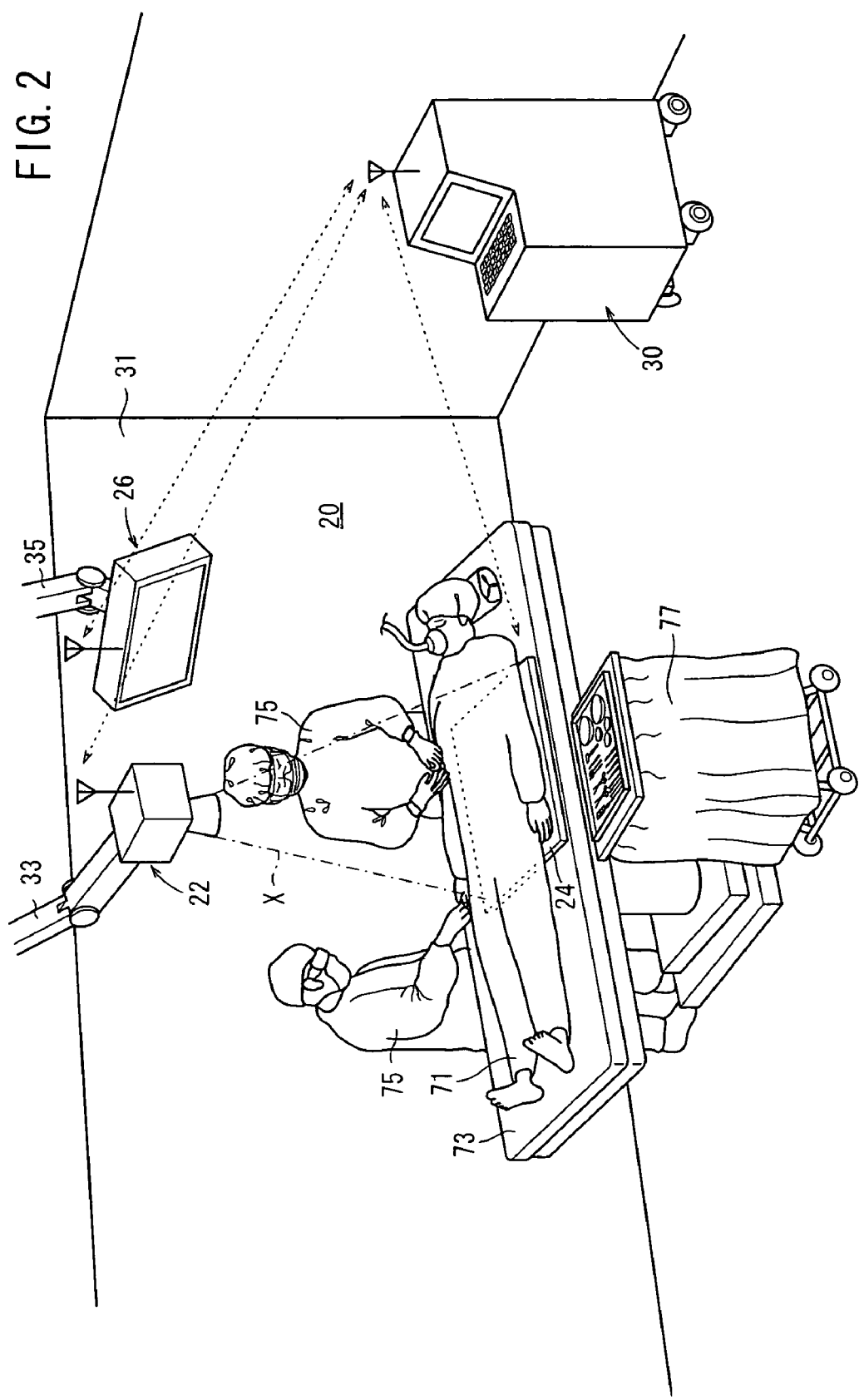
FIG. 2 is a perspective view of an operating room incorporating a radiation image capturing system included in the radiation information system shown in FIG. 1.

FIG. 2 shows in perspective an operating room 31, which serves as an image capturing room, incorporating one of the image capturing systems 20 according to the present embodiment. As shown in FIG. 2, the operating room 31 has, in addition to the image capturing system 20, a surgical table 73 for the patient 71 to lie thereon, and an instrument table 77 disposed on one side of the surgical table 73 for placing thereon various tools and instruments to be used by the surgeons 75 for operating the patient 71. The surgical table 73 is surrounded by various apparatus required for surgical operations, including an anesthesia apparatus, an aspirator, an electrocardiograph, a blood pressure monitor, etc., which are omitted from illustration in FIG. 2.

The image capturing apparatus 22 is coupled to a universal arm 33 so as to be movable to a desired position for capturing a desired area of the patient 71 and also to be retractable to a position out of the way while the surgeons 75 are performing a surgical operation on the patient 71. Similarly, the display device 26 is coupled to a universal arm 35 so as to be movable to a position where the surgeons 75 can easily confirm a captured radiation image displayed on the display device 26.

In FIG. 2, the image capturing apparatus 22 is illustrated as being located in the operating room 31. However, the image capturing apparatus 22 may be located in any of various other places, e.g., an image capturing room which is dedicated to capturing radiation images.

Figure 3:
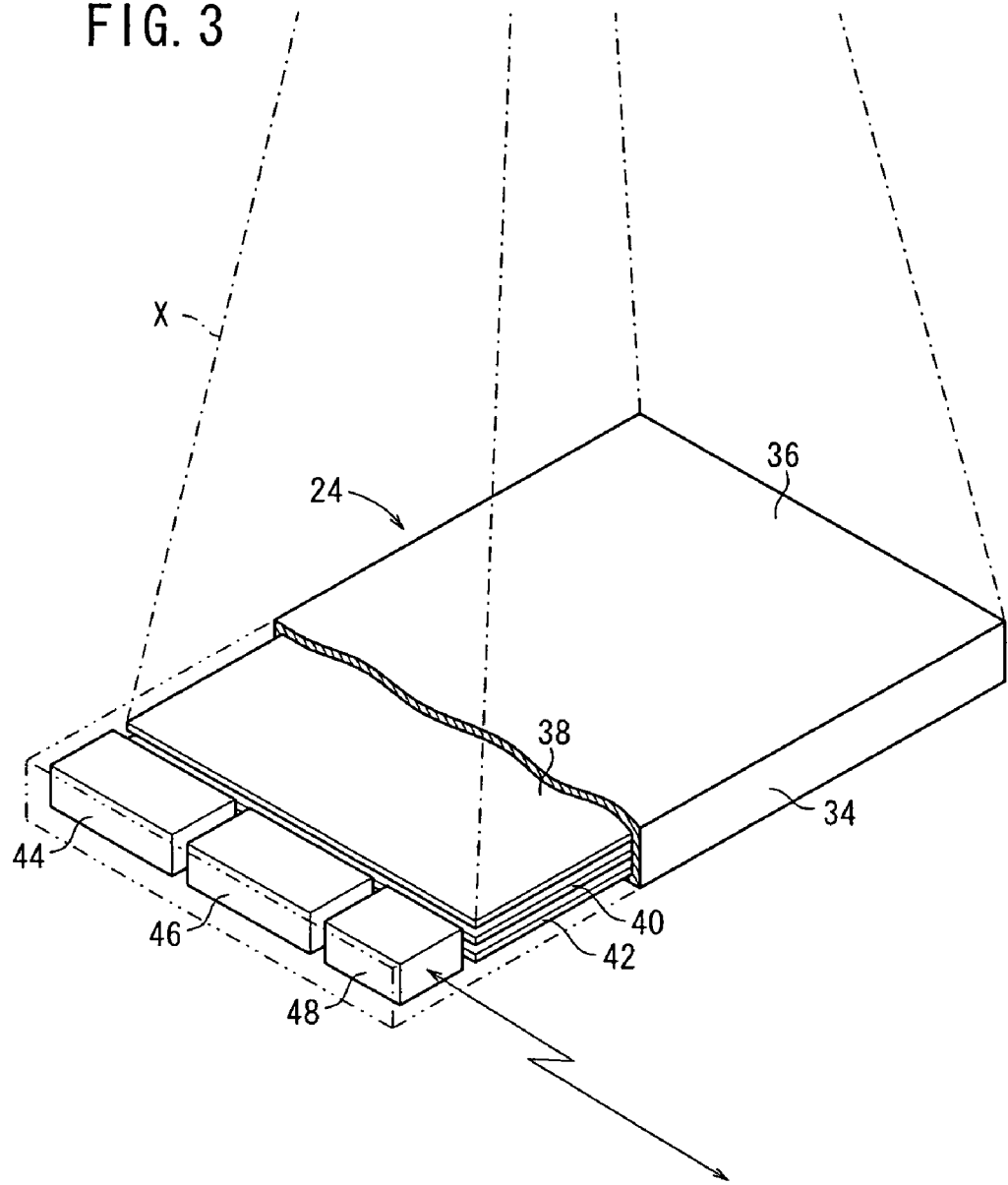
FIG. 3 is a perspective view, partly cut away, showing internal structural details of a radiation detecting cassette used in the radiation image capturing system.

(b) Cassette 24:

FIG. 3 shows internal structural details of the cassette 24. As shown in FIG. 3, the cassette 24 has a casing 34 made of a material permeable to the radiation X. The casing 34 houses therein a grid 38 for removing scattered rays of the radiation X from the patient 71, a radiation detector (radiation conversion panel) 40 for detecting the radiation X that has passed through the patient 71, and a lead plate 42 for absorbing back scattered rays of the radiation X, which are successively arranged in the order named from a surface 36 of the casing 34 which is irradiated with the radiation X. The irradiated surface 36 of the casing 34 may be constructed as the grid 38.

The casing 34 also houses therein a battery 44 as a power supply of the radiation detecting cassette 24, a cassette controller 46 for energizing the radiation detector 40 with electric power supplied from the battery 44, and a transceiver 48 for sending and receiving signals including the information of the radiation X detected by the radiation detector 40, to and from the console 30. The cassette controller 46 stores a cassette ID unique to the cassette 24.

When the cassette 24 is used in the operating room 31 or the like, the cassette 24 may be subjected to adhesion of blood, contamination, etc. However, when the cassette 24 is designed to have a waterproof and hermetically-sealed structure, and is sterilized and cleaned as necessary, one cassette 24 can be used repeatedly.

The cassette 24 is not limited to use in the operating room 31, and may be used for a medical examination and a round in the hospital.

Also, the cassette 24 may communicate with external devices via optical wireless communication using infrared light or the like, instead of general wireless communication using radio wave.

Figure 4:
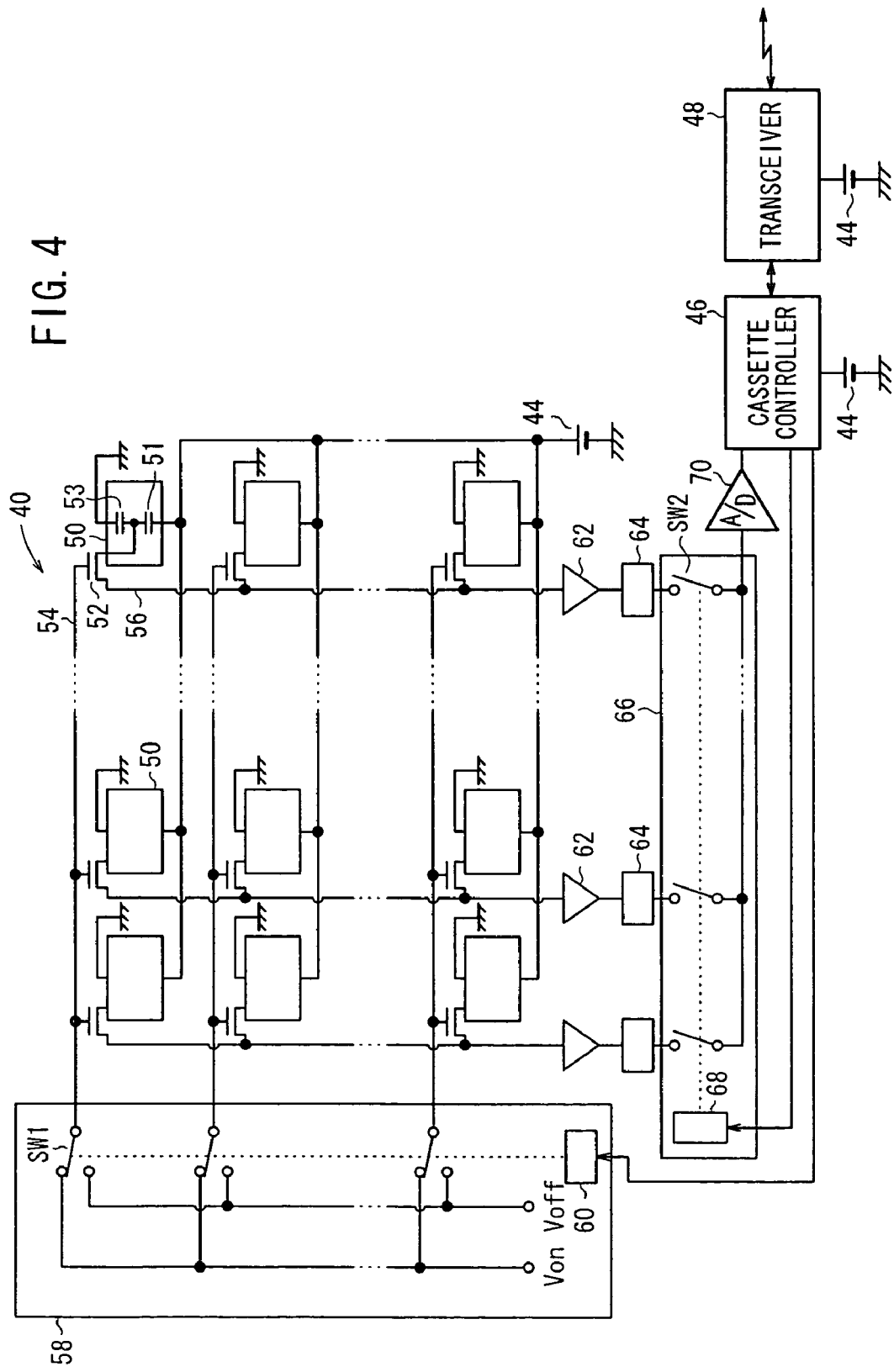
FIG. 4 is a block diagram of a circuit arrangement of a radiation detector of the radiation detecting cassette.

(c) Radiation Detector 40:

FIG. 4 shows in block form a circuit arrangement of the radiation detector 40. As shown in FIG. 4, the radiation detector 40 comprises an array of thin-film transistors (TFTs) 52 arranged in rows and columns, a photoelectric conversion layer 51 made of a material such as amorphous selenium (a-Se) for generating electric charges upon detection of the radiation X, the photoelectric conversion layer 51 being disposed on the array of TFTs 52, and an array of storage capacitors 53 connected to the photoelectric conversion layer 51. When the radiation X is applied to the radiation detector 40, the photoelectric conversion layer 51 generates electric charges, and the storage capacitors 53 store the generated electric charges. Then, the TFTs 52 are turned on along each row at a time to read the electric charges from the storage capacitors 53 as an image signal. In FIG. 4, the photoelectric conversion layer 51 and one of the storage capacitors 53 are shown as a pixel 50, and the pixel 50 is connected to one of the TFTs 52. Details of the other pixels 50 are omitted from illustration. Since amorphous selenium tends to change its structure and lose its function at high temperatures, it needs to be used in a certain temperature range. Therefore, some means for cooling the radiation detector 40 should preferably be provided in the radiation detecting cassette 24.

The TFTs 52 connected to the respective pixels 50 are connected to respective gate lines 54 extending parallel to the rows and respective signal lines 56 extending parallel to the columns. The gate lines 54 are connected to a line scanning driver 58, and the signal lines 56 are connected to a multiplexer 66 serving as a reading circuit.

The gate lines 54 are supplied with control signals Von, Voff for turning on and off the TFTs 52 along the rows from the line scanning driver 58. The line scanning driver 58 comprises a plurality of switches SW1 for switching between the gate lines 54 and an address decoder 60 for outputting a selection signal for selecting one of the switches SW1 at a time. The address decoder 60 is supplied with an address signal from the cassette controller 46.

The signal lines 56 are supplied with electric charges stored in the storage capacitors 53 of the pixels 50 through the TFTs 52 arranged in the columns. The electric charges supplied to the signal lines 56 are amplified by amplifiers 62 connected respectively to the signal lines 56. The amplifiers 62 are connected through respective sample and hold circuits 64 to the multiplexer 66. The multiplexer 66 comprises a plurality of switches SW2 for successively switching between the signal lines 56 and an address decoder 68 for outputting a selection signal for selecting one of the switches SW2 at a time. The address decoder 68 is supplied with an address signal from the cassette controller 46. The multiplexer 66 has an output terminal connected to an A/D converter 70. A radiation image signal generated by the multiplexer 66 based on the electric charges from the sample and hold circuits 64 is converted by the A/D converter 70 into a digital image signal representing radiation image information, which is supplied to the cassette controller 46.

Figure 5:
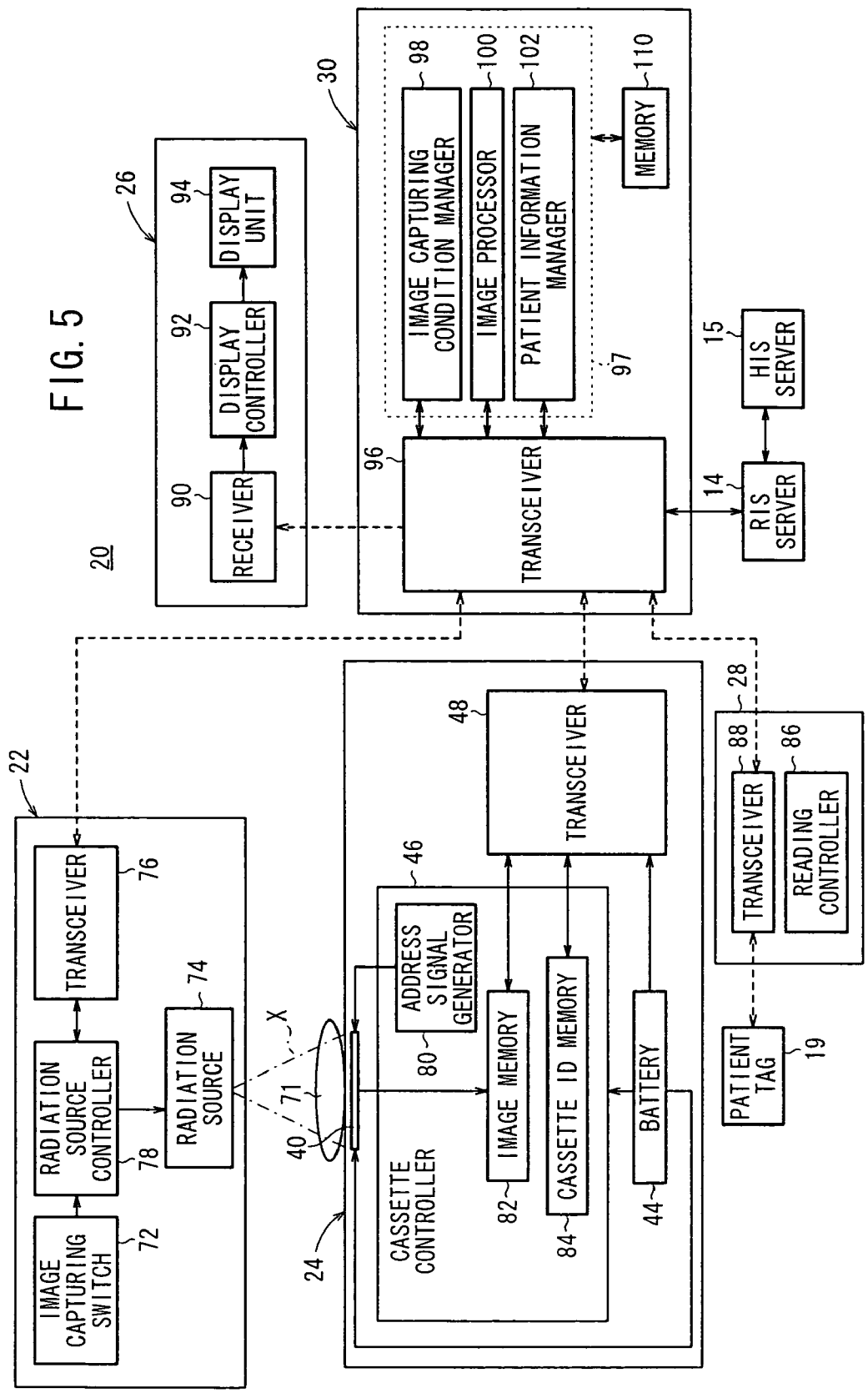
FIG. 5 is a block diagram of the radiation image capturing system according to the first embodiment.

(d) Configurational Details of the Radiation Image Capturing System 20:

FIG. 5 shows in block form configurational details of each of the radiation image capturing systems 20.

As shown in FIG. 5, the image capturing apparatus 22 comprises an image capturing switch 72, a radiation source 74 for outputting the radiation X, a transceiver 76 for receiving a signal representing image capturing conditions from the console 30 by way of wireless communications and transmitting a signal such as an image capturing completion signal, etc. to the console 30 by way of wireless communications, and a radiation source controller 78 for controlling the radiation source 74 based on an image capturing start signal supplied from the image capturing switch 72 and image capturing conditions supplied from the transceiver 76.

The radiation source controller 78 acquires image capturing conditions for the patient 71 from a console controller 97 (described later) of the console 30 through a transceiver 96 (described later) of the console 30 and the transceiver 76 of the image capturing apparatus 22 by way of wireless communications, and controls the radiation source 74 according to the acquired image capturing conditions to apply a radiation X at a desired dose to the patient 71.

The radiation detecting cassette 24 houses therein the radiation detector 40, the battery 44, the cassette controller 46, and the transceiver 48. The cassette controller 46 comprises an address signal generator 80 for supplying address signals to the address decoder 60 of the line scanning driver 58 (FIG. 4) and the address decoder 68 of the multiplexer 66, of the radiation detector 40, an image memory 82 for storing the radiation image information detected by the radiation detector 40, and a cassette ID memory 84 for storing cassette ID for identifying the radiation detecting cassette 24. The transceiver 48 receives a transmission request signal from the console 30 by way of wireless communications and transmits the cassette ID stored in the cassette ID memory 84 and the radiation image information stored in the image memory 82 to the console 30 by way of wireless communications.

The display device 26 comprises a receiver 90 for receiving radiation image information from the console 30, a display controller 92 for controlling the display of the received radiation image information, and a display unit 94 for displaying the radiation image information processed by the display controller 92.

The patient ID reader 28 comprises a reading controller 86 and a transceiver 88. The reading controller 86 sends a patient ID request signal through the transceiver 88 to the patient tag 19 by way of wireless communications, and receives the patient ID which is transmitted from the patient tag 19 in response to the patient ID request signal. The reading controller 86 also sends the received patient ID through the transceiver 88 to the console 30 by way of wireless communications. The patient ID reader 28 is located near the entrance/exit of the operating room 31, for example.

The console 30 comprises a transceiver 96, a console controller 97, and a memory 110. The transceiver 96 transmits and receives various information including radiation image information by way of wireless communications. The console controller 97 controls operation of the console 30. The console controller 97 comprises an image capturing condition manager 98 for managing image capturing conditions required for the image capturing apparatus 22 to capture radiation images, an image processor 100 for processing radiation image information transmitted from the radiation detecting cassette 24, and a patient information manager 102 for managing patient information of the patient 71 whose images are to be captured.

The image capturing conditions refer to condition required for determining image capturing details including an area to be imaged, an angle at which the area is to be imaged, the number of radiation images to be captured, a tube voltage, a tube current, an irradiation time, etc. required to apply a radiation X at an appropriate dose to an area to be imaged of the patient 71, the cassette ID, size, sensitivity, etc. of the cassette 24.

The patient information refers to information about the patient 71 required to capture radiation images thereof, including attribute information of the patient 71 (name, gender, age, patient ID, etc.), a history of radiation images captured in the past, etc.

The image capturing condition manager 98 checks the cassette ID (hereinafter also referred to as "specified cassette ID") of a cassette 24 which is specified by the RIS server 14 as a cassette 24 that is planned to be used to capture a radiation image, and the cassette ID (hereinafter also referred to as "actual cassette ID") of a cassette 24 which is read by the console 30 as a cassette 24 that is actually used to capture a radiation image, against each other, and determines whether to permit the capturing of a radiation image or not based on the result of the cassette ID check.

The patient information manager 102 checks the patient ID (hereinafter also referred to as "specified patient ID") which is specified by the RIS server 14 as the patient ID of a patient 71 that is planned to be imaged, and the patient ID (hereinafter also referred to as "actual patient ID") which is read by the patient ID reader 28 from the patient tag 19 of the patient 71 that is to be actually imaged, against each other, and determines whether to permit the capturing of a radiation image or not based on the result of the patient ID check.

The memory 110 stores the cassette ID, the specifications of the cassette 24, the patient ID, and the radiation image information processed by the image processor 100.

(e) Process for Capturing a Radiation Image with the Image Capturing System 20:

The radiation X which has passed through the patient 71 is applied to the grid 38 of the radiation detecting cassette 24, which removes scattered rays of the radiation X. Then, the radiation X is applied to the radiation detector 40, and converted into electric signals by the photoelectric conversion layer 51 of the pixels 50 of the radiation detector 40. The electric signals are stored as electric charges in the storage capacitors 53 (see FIG. 4). The stored electric charges, which represent radiation image information of the patient 71, are read from the storage capacitors 53 according to address signals which are supplied from the address signal generator 80 of the cassette controller 46 to the line scanning driver 58 and the multiplexer 66.

Specifically, in response to the address signal supplied from the address signal generator 80, the address decoder 60 of the line scanning driver 58 outputs a selection signal to select one of the switches SW1, which supplies the control signal Von to the gates of the TFTs 52 connected to the gate line 54 corresponding to the selected switch SW1. In response to the address signal supplied from the address signal generator 80, the address decoder 68 of the multiplexer 66 outputs a selection signal to successively turn on the switches SW2 to switch between the signal lines 56 for thereby reading radiation image information represented by the electric charges stored in the storage capacitors 53 of the pixels 50 connected to the selected gate line 54, through the signal lines 56.

The radiation image information (electric charges) read from the storage capacitors 53 of the pixels 50 connected to the selected gate line 54 are amplified by the respective amplifiers 62, sampled by the sample and hold circuits 64, and supplied to the multiplexer 66. Based on the supplied electric charges, the multiplexer 66 generates and supplies a radiation image signal to the A/D converter 70, which converts the radiation image signal into a digital signal. The digital signal which represents the radiation image information is stored in the image memory 82 of the cassette controller 46. The stored digital signal is transmitted through the transceiver 48 to the console 30 by way of wireless communications.

Similarly, the address decoder 60 of the line scanning driver 58 successively turns on the switches SW1 to switch between the gate lines 54 according to the address signal supplied from the address signal generator 80. The electric charges, serving as radiation image information, stored in the storage capacitors 53 of the pixels 50 connected to the successively selected gate lines 54 are read through the signal lines 56, and processed by the multiplexer 66 and the A/D converter 70 into digital signals, which are stored in the image memory 82 of the cassette controller 46.

The radiation image information transmitted to the console 30 is received by the transceiver 96, processed by the image processor 100, and then stored in the memory 110 in association with the patient information of the patient 71 registered in the patient information manager 102.

The radiation image information processed by the image processor 100 is transmitted from the transceiver 96 to the display device 26. In the display device 26, the receiver 90 receives the radiation image information, and the display controller 92 controls the display unit 94 to display a detailed radiation image based on the radiation image information.

The surgeons 75 perform a surgical operation on the patient 71 while watching the radiation image displayed on the display unit 94.

Since no cables for transmitting and receiving signals are connected between the image capturing apparatus 22, the radiation detecting cassette 24, the display device 26, and the patient ID reader 28, and the console 30, no such cables are placed on the floor of the operating room 31 and hence there are no cable-induced obstacles to the operation performed by the surgeons 75, the radiological technician, or other staff members in the operating room 31.

2. Operation of the First Embodiment

The RIS 10 according to the first embodiment is basically constructed as described above. Operation of the RIS 10 will be described below with reference to FIG. 6.

For an easier understanding of the present invention, it is assumed that the radiation image capturing system 20 is not installed in the operating room 31 shown in FIG. 2, but in an image capturing room which is dedicated to capturing radiation images.

Figure 6:
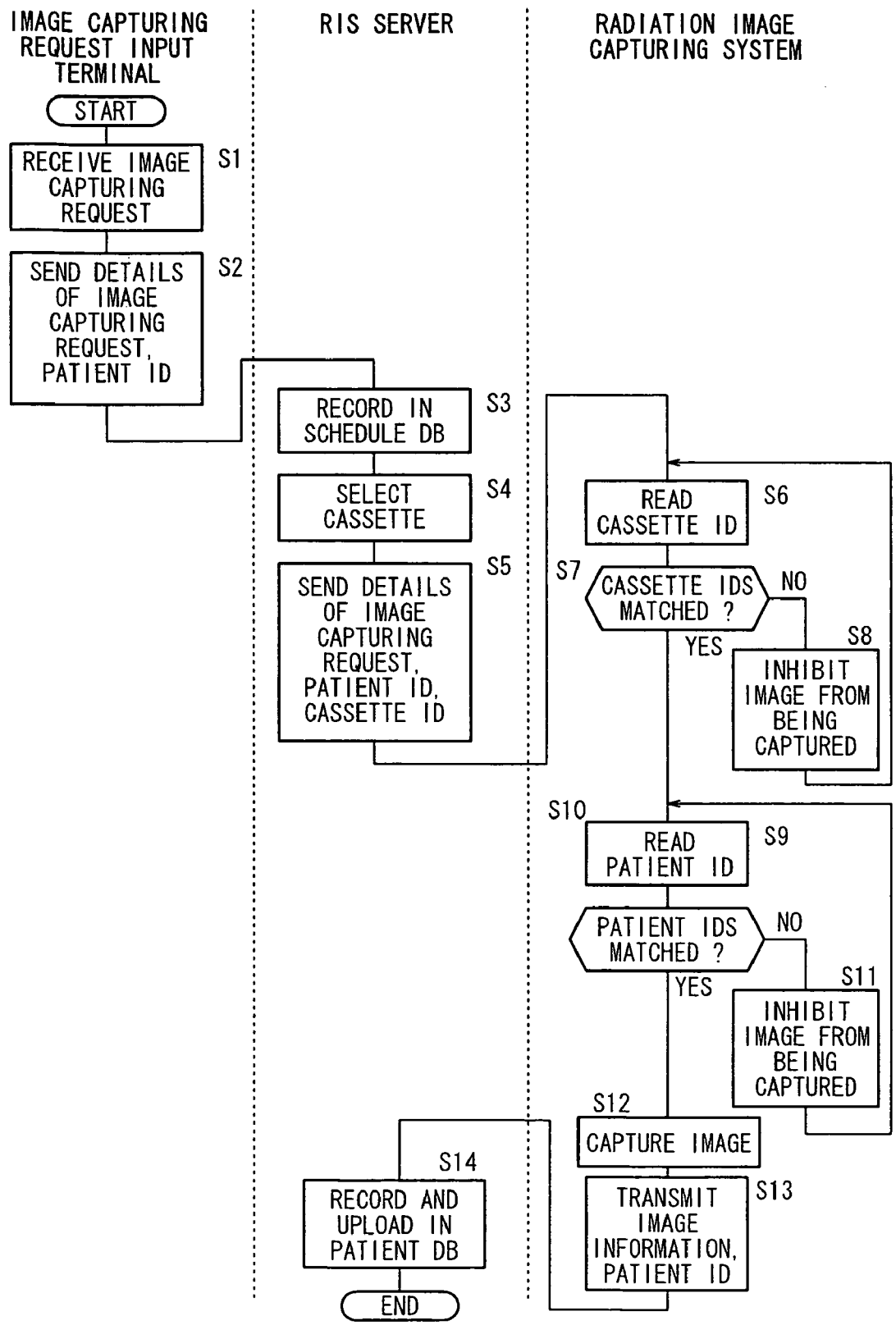
FIG. 6 is a flowchart of an operation sequence of the radiation information system according to the first embodiment.

In step S1 shown in FIG. 6, the image capturing request input terminal 12 receives an image capturing request from one of the surgeons 75 or the radiological technician. The image capturing request specifies the date on which a radiation image is to be captured and image capturing conditions including an area to be imaged, an angle at which the area is to be imaged, the number of radiation images to be captured, a tube voltage, a tube current, an irradiation time, etc. required to apply a radiation X, and specifications of the cassette 24 including the size and sensitivity of the cassette 24. If the cassette DB 17 of the RIS server 14 has stored therein input items in association with each other, e.g., the area to be imaged, the specifications of the cassette 24, and other image capturing conditions in association with other, then the image capturing request may represent fewer specified image capturing conditions. The image capturing request is related to the patient ID of the patient 71 whose image is to be captured. When the surgeons 75 or the radiological technician enters the image capturing request, the surgeons 75 or the radiological technician confirms bookings that have already been made for the radiation image capturing system 20 by referring to the schedule DB 18 of the RIS server 14.

In step S2, the image capturing request input terminal 12 sends the details of the received image capturing request (including the specifications of the cassette 24) and the patient ID to the RIS server 14.

In step S3, the RIS server 14 records the details of the image capturing request (the date on which a radiation image is to be captured and the image capturing conditions) and the patient ID sent from the image capturing request input terminal 12, in the schedule DB 18. If the cassette DB 17 has stored therein input items in association with each other, as described above, then the associated input items are also recorded in the schedule DB 18.

In step S4, the RIS server 14 selects a cassette 24 which meet the image capturing conditions by referring to the cassette DB 17, and records the cassette ID of the selected cassette 24 in the schedule DB 18.

The details of the data stored in the schedule DB 18 can be confirmed at any time on the console 30 of the radiation image capturing system 20. Stated otherwise, when steps S3, S4 are carried out, if the console 30 is accessing the schedule DB 18 of the RIS server 14, then the RIS server 14 supplies the combination of the details of the image capturing request, the patient ID, and the cassette ID to the condole 30 (i.e., the console 30 downloads the combination thereof), in step S5. If a radiation image should be captured immediately, then the RIS server 14 may send the details of the image capturing request, etc. proactively on its own initiative to the console 30. Since the usage of the cassette 24 varies from time to time, it may be possible not to supply the cassette ID until immediately before a radiation image starts to be taken.

Based on a schedule supplied from the RIS server 14, the radiological technician captures a radiation image of the patient 71. The schedule is displayed on a display monitor of the console 30. Before a first radiation image starts being captured, the radiological technician identifies a cassette 24 to be used to capture the first radiation image, based on the display on the console 30, and sets the cassette 24 in a given position in the image capturing room. The console 30 then establishes wireless communications with the installed cassette 24, and reads the cassette ID from the cassette 24 in step S6. For establishing wireless communications between the console 30 and the installed cassette 24, the console 30 keeps sending a cassette ID request signal with a predetermined radio-wave intensity, which may be strong enough to establish wireless communications within a radius of 3 m from the console 30, for example, until the cassette 24 responds. When the cassette 24 responds, wireless communications are established between the console 30 and the installed cassette 24.

In step S7, the image capturing condition manager 98 (FIG. 5) of the console 30 (identifying unit) checks the cassette ID (specified cassette ID) of a cassette 24 which is specified by the RIS server 14 as a cassette 24 that is planned to be used to capture a radiation image, and the cassette ID (actual cassette ID) of a cassette 24 which is read by the console 30 from a cassette 24 that is actually placed in the image capturing room, against each other.

If the specified cassette ID and the actual cassette ID do not match each other, then the console 30 does not permit the image capturing apparatus 22 to apply the radiation X in step S8. Specifically, the image capturing condition manager 98 of the console 30 sends a signal for inhibiting the radiation source 74 from applying the radiation X, to the radiation source controller 78 of the image capturing apparatus 22. The console 30 displays a message indicative of the inhibition of the application of the radiation X on its display monitor, after which control goes back to step S6. If the specified cassette ID and the actual cassette ID match each other, then control goes to step S9.

Based on the display on the console 30, the radiological technician identifies the patient 71 to be imaged first, and calls the identified patient 71 into the image capturing room. When the identified patient 71 goes into the image capturing room, the patient ID reader 28 located near the entrance/exit of the image capturing room reads the patient ID of the patient 71 from the patient tag 19 thereof by way of wireless communications, and sends the read patient ID to the console 30 in step S9.

In step S10, the patient information manager 102 of the console 30 checks the patient ID (specified patient ID) which is specified by the RIS server 14 as the patient ID of a patient 71 that is planned to be imaged, and the patient ID (actual patient ID) which is read by the patient ID reader 28 from the patient tag 19 of the patient 71 that has actually gone into the image capturing room, against each other.

If the specified patient ID and the actual patient ID do not match each other, then the console 30 does not permit the image capturing apparatus 22 to apply the radiation X in step S11. Specifically, the patient information manager 102 of the console 30 sends a signal for inhibiting the radiation source 74 from applying the radiation X, to the radiation source controller 78 of the image capturing apparatus 22. The console 30 displays a message indicative of the inhibition of the application of the radiation X on its display monitor, after which control goes back to step S9. If the specified patient ID and the actual patient ID match each other, then the console 30 permits the image capturing apparatus 22 to apply the radiation X to capture a radiation image of the patient 71 in step S12.

The steps S6 through S8 and the steps S9 through S11 may be switched around, or may be carried out concurrently.

If the specified patient ID and the actual patient ID do not match each other, but if the combination of the actual patient ID and the actual cassette ID is proper, or in other words, if the order of patients to be imaged is wrong, but if the details of the image capturing request are satisfactory, then the console 30 may permit the image capturing apparatus 22 to apply the radiation X to capture a radiation image of the patient 71.

When the capturing of the radiation image is completed in step S12, the radiation image information acquired by the cassette 24 is sent to the console 30, which transmits the received radiation image information and the corresponding patient ID to the RIS server 14 in step S13. The RIS server 14 stores the received radiation image information in association with the patient ID in the patient DB 16 in step S14. The radiation image information stored in the patient DB 16 can be viewed from the image capturing request input terminal 12.

3. Advantages of the First Embodiment

According to the first embodiment, as described above, the console 30 reads the cassette ID stored in the cassette 24, checks the read cassette ID (actual cassette ID) against the specified cassette ID sent from the RIS server 14, and determines whether to permit the capturing of a radiation image or not based on the result of the cassette ID check. Since the cassette ID is read from the cassette 24 itself, the cassette ID is reliably detected. As the console 30 checks the actual cassette ID against the specified cassette ID, the cassette 24 is reliably prevented from being mistaken.

Furthermore, the actual cassette ID is read from the cassette 24 into the console 30 by way of wireless communications. Consequently, the actual cassette ID is read with ease.

Moreover, if the console 30 judges that the capturing of a radiation image is not to be permitted, then it inhibits the radiation source 74 from applying the radiation X to the patient 71. Therefore, if the console 30 judges that the capturing of a radiation image should not be permitted, the radiation X is automatically inhibited from being applied to the patient 71 for higher safety.

In addition, the console 30 checks the specified patient ID supplied from the RIS server 14 and the actual patient ID read from the patient tag 19 against each other, and determines whether to permit the capturing of a radiation image or not based on the result of the patient ID check. As a result, the patient 71 is reliably prevented from being mistaken.

The radiation image capturing system 20 is easy and efficient to use because it is managed as part of the RIS 10 which includes the image capturing request input terminals 12 and the RIS server 14. Since the cassette IDs and the patient IDs are managed altogether by the RIS server 14, the radiation image capturing system 20 can also be used easily and efficiently.

B. 2nd Embodiment

1. Differences with the First Embodiment

Figure 7:
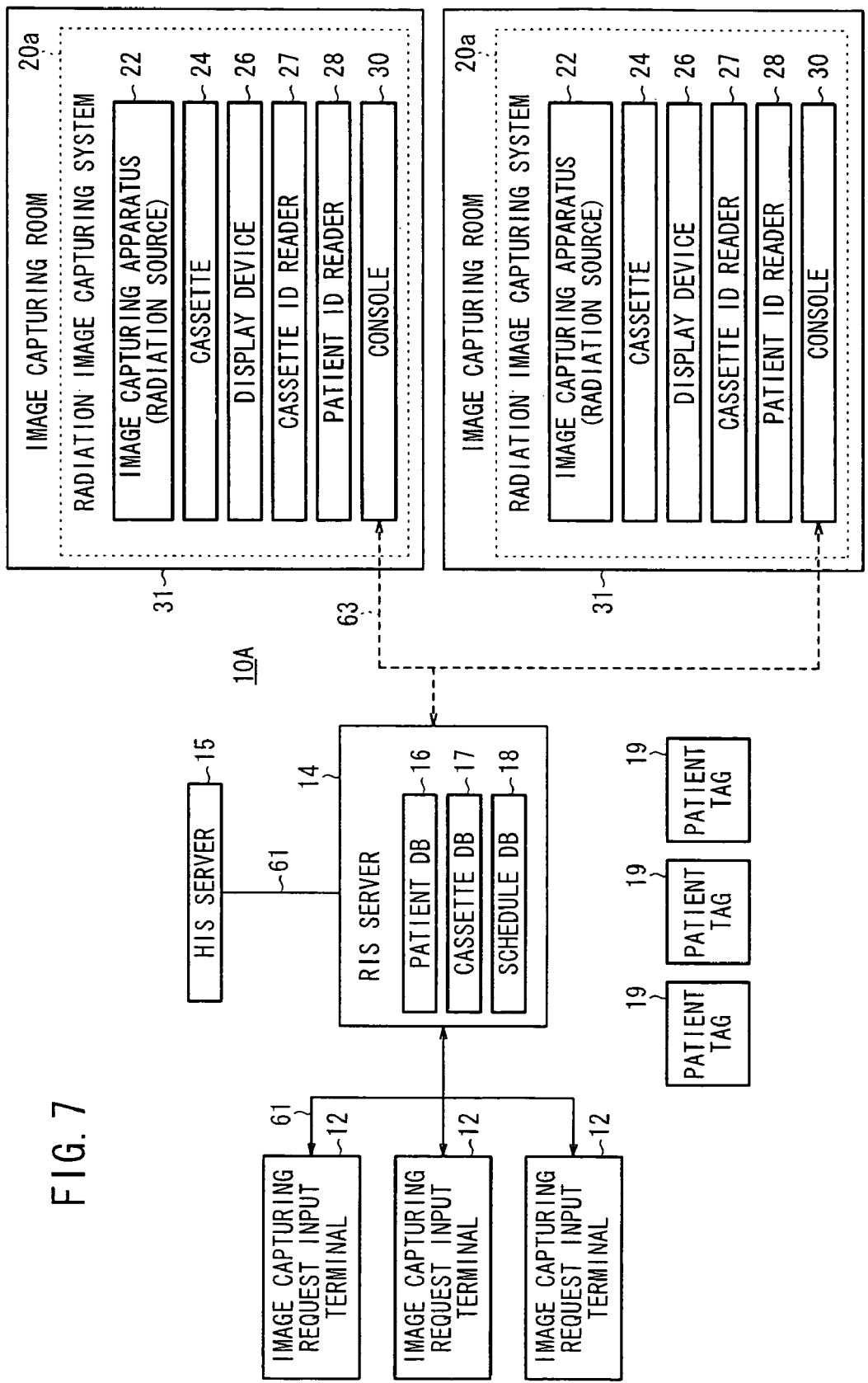
FIG. 7 is a block diagram of a radiation information system according to a second embodiment of the present invention.

FIG. 7 is a block diagram showing the components of a radiation information system 10A (hereinafter also referred to as "RIS 10A") according to a second embodiment of the present invention. The RIS 10A is basically the same as the RIS 10 according to the first embodiment, except that each of radiation image capturing systems 20a (hereinafter also referred to as "image capturing systems 20a") additionally includes a cassette ID reader 27 for reading the cassette ID from a cassette 24 by way of wireless communications. As with the image capturing apparatus 22, the cassette 24, the display device 26, and the patient ID reader 28, the cassette ID reader 27 is capable of sending and receiving signals to and from the console 30 by way of wireless communications.

Figure 8:
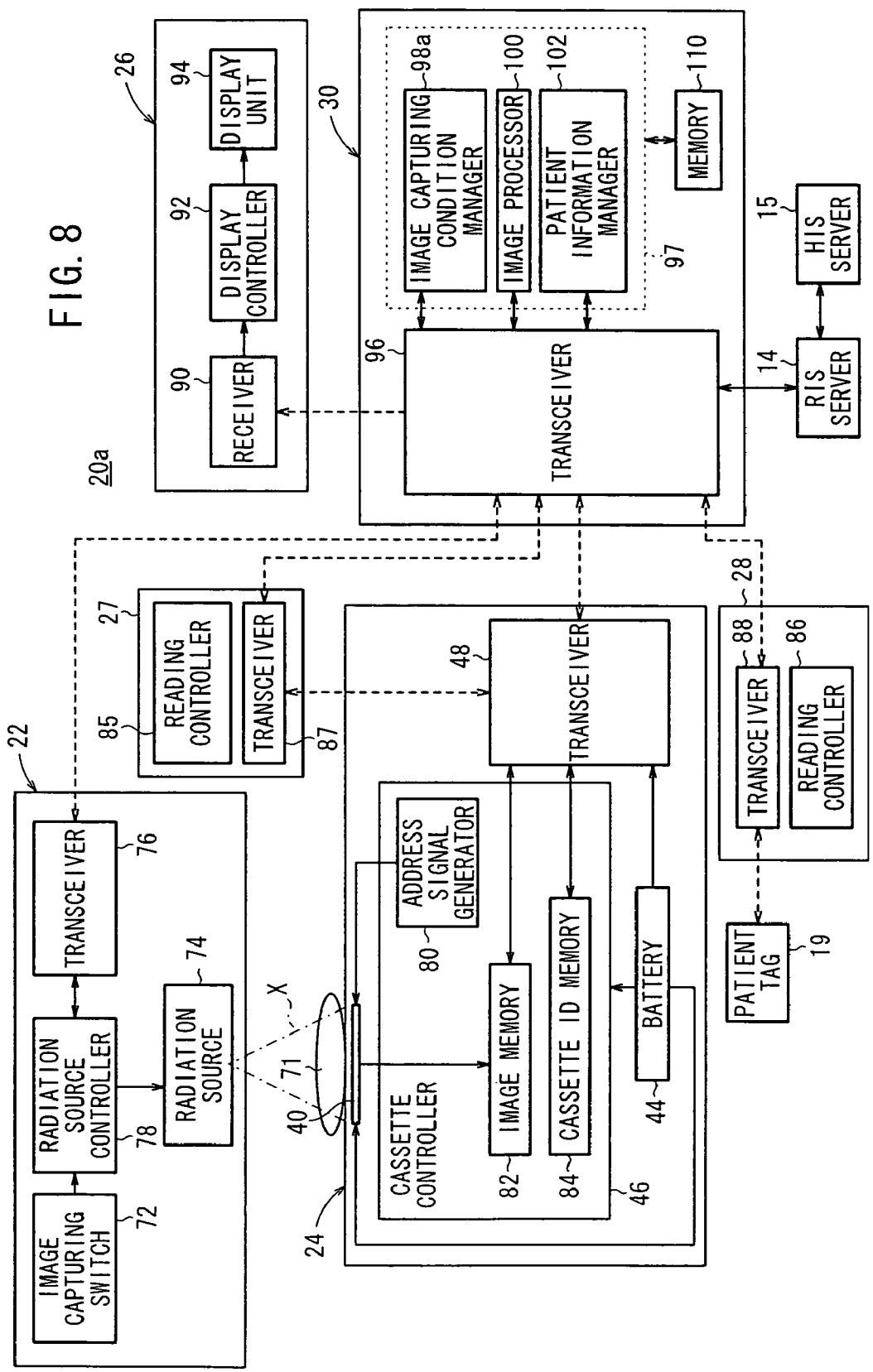
FIG. 8 is a block diagram of a radiation image capturing system according to the second embodiment.

As shown in FIG. 8, the cassette ID reader 27 comprises a reading controller 85 and a transceiver 87. The reading controller 85 sends a cassette ID request signal through the transceiver 87 to the cassette 24 by way of wireless communications, and receives a cassette ID that is sent from the cassette 24 in response to the cassette ID request signal. The reading controller 85 sends the received cassette ID through the transceiver 87 to the console 30 by way of wireless communications. The cassette ID reader 27 is located near the entrance/exit of the operating room 31, for example.

The console 30 has an image capturing condition manager 98a which compares the specifications (hereinafter referred to as "requisite specifications") of a cassette 24 indicated from the RIS server 14 as a cassette 24 that is planned to be used to capture a radiation image, and the specifications (hereinafter referred to as "actual specifications") of a cassette 24 whose cassette ID is read by the cassette ID reader 27 as indicating a cassette 24 that is actually used to capture a radiation image, with each other, determines whether the actual specifications match the requisite specifications or not, and determines whether to permit the capturing of a radiation image or not based on the result of the cassette specifications comparison.

2. Operation of the Second Embodiment

The RIS 10A according to the second embodiment is basically constructed as described above. Operation of the RIS 10A will be described below with reference to FIGS. 9 and 10.

For an easier understanding of the present invention, it is assumed that the radiation image capturing system 20a is not installed in the operating room 31 shown in FIG. 2, but in an image capturing room which is dedicated to capturing radiation images.

Figure 9:
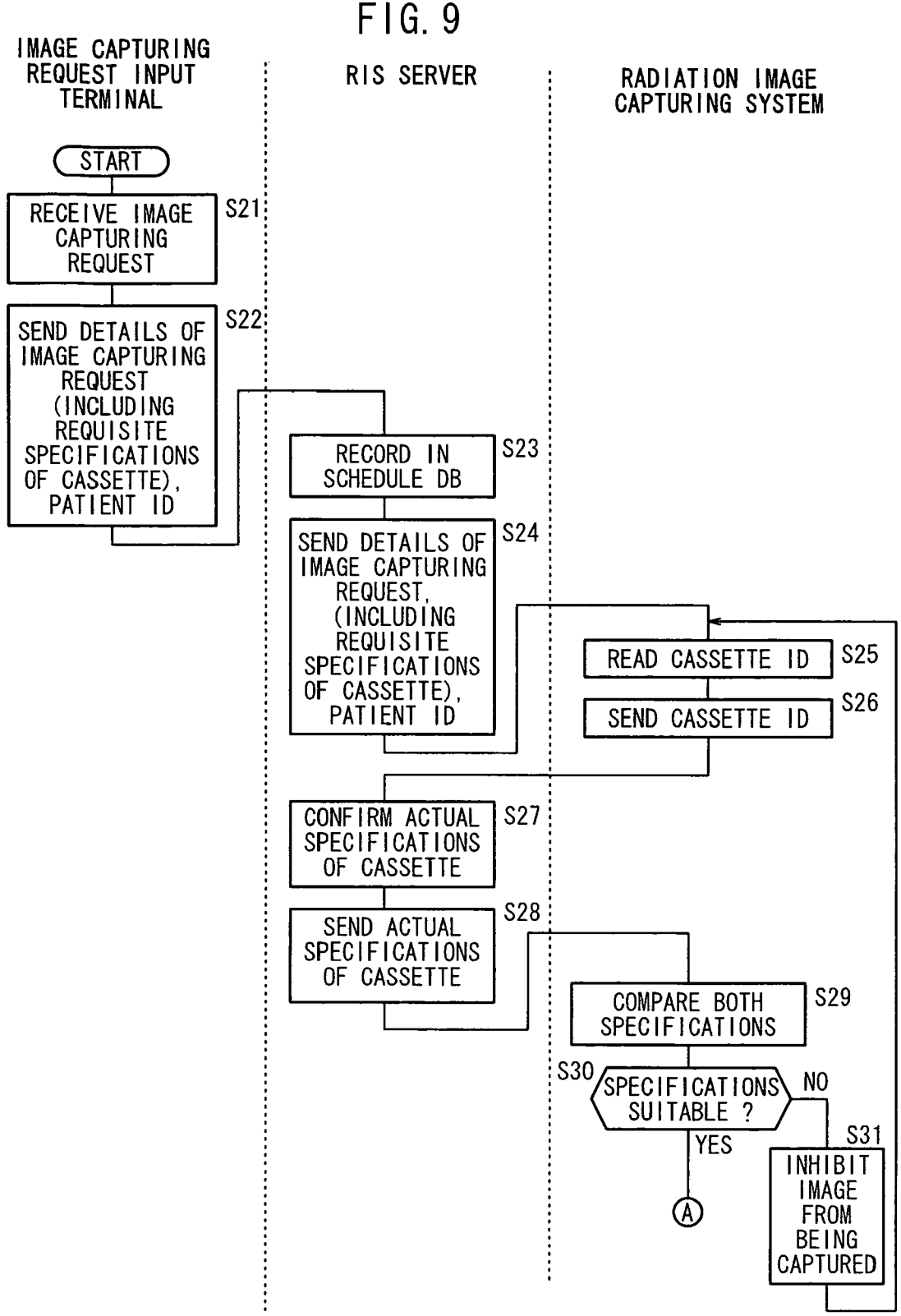
FIG. 9 is a flowchart of a part of an operation sequence of the radiation information system according to the second embodiment.

In step S21 shown in FIG. 9, the image capturing request input terminal 12 receives an image capturing request from one of the surgeons 75 or the radiological technician. The image capturing request specifies the date on which a radiation image is to be captured and image capturing conditions including an area to be imaged, an angle at which the area is to be imaged, the number of radiation images to be captured, a tube voltage, a tube current, an irradiation time, etc. required to apply a radiation X, and the size and sensitivity (requisite specifications) of the cassette 24 (radiation detector 40). If the cassette DB 17 of the RIS server 14 has stored therein input items in association with each other, e.g., the area to be imaged, the specifications of the cassette 24, and other image capturing conditions in association with each other, then the image capturing request may represent fewer specified image capturing conditions. The image capturing request is related to the patient ID of the patient 71 whose image is to be captured. When the surgeons 75 or the radiological technician enters the image capturing request, the surgeons 75 or the radiological technician confirms bookings that have already been made for the radiation image capturing system 20a by referring to the schedule DB 18 of the RIS server 14.

In step S22, the image capturing request input terminal 12 sends the details of the received image capturing request (including the requisite specifications of the cassette 24) and the patient ID to the RIS server 14.

In step S23, the RIS server 14 records the details of the image capturing request (the date on which a radiation image is to be captured and the image capturing conditions) and the patient ID sent from the image capturing request input terminal 12, in the schedule DB 18. If the cassette DB 17 has stored therein input items in association with each other, as described above, then the associated input items are also recorded in the schedule DB 18.

The details of the data recorded in the schedule DB 18 can be confirmed at any time on the console 30 of the radiation image capturing system 20a. Stated otherwise, when step S23 is carried out, if the console 30 is accessing the schedule DB 18 of the RIS server 14, then the RIS server 14 supplies the combination of the details (including the requisite specifications of the cassette 24) of the image capturing request and the patient ID, to the condole 30 (i.e., the console 30 downloads the combination thereof), in step S24. If a radiation image should be captured immediately, then the RIS server 14 may send the details of the image capturing request, etc. proactively on its own initiative to the console 30.

Based on a schedule supplied from the RIS server 14, the radiological technician captures a radiation image of the patient 71. The schedule is displayed on the display monitor of the console 30. Before a first radiation image starts being captured, the radiological technician identifies a cassette 24 to be used to capture the first radiation image, based on the display on the console 30, i.e., the requisite specifications of the cassette 24. When each cassette 24 is not in use, it is placed outside of the image capturing room and kept in a power saving mode. In the power saving mode, the cassette controller 46 is capable of receiving certain external signals, but the radiation detector 40 is not supplied with electric power and is unable to detect a radiation. When the radiological technician brings the selected cassette 24 into the image capturing room, the cassette ID reader 27 reads the cassette ID of the cassette 24 in step S25. In order for the cassette ID reader 27 to read the cassette ID from the cassette 24, the cassette ID reader 27 keeps sending a cassette ID request signal with a predetermined radio-wave intensity, which may be strong enough to establish wireless communications within a radius of 1 m from the cassette ID reader 27, for example, until the cassette 24 responds. When the cassette 24 (cassette controller 46) receives the cassette ID request signal from the cassette ID reader 27, the cassette 24 switches from the power saving mode to a normal mode in which the radiation detector 40 is supplied with electric power and is able to detect a radiation.

In step S26, the cassette ID reader 27 sends the read cassette ID to the console 30, which sends the received cassette ID to the RIS server 14.

In step S27, the RIS server 14 reads the specifications (actual specifications) of the cassette 24 that is associated with the cassette ID sent from the console 30, from the cassette DB 17. In step S28, the RIS server 14 sends the read actual specifications to the console 30. In step S29, the image capturing condition manager 98a of the console 30 compares the specifications (requisite specifications) of the cassette 24 which is indicated by the RIS server 14 as a cassette 24 that is planned to be used to capture a radiation image, and the specifications (actual specifications) of a cassette 24 which corresponds to the cassette ID that is read by the cassette ID reader 27 from the cassette 24 which is actually placed in the image capturing room, with each other, and determines whether the actual specifications are appropriate or not, i.e., whether the actual specifications are the same as or better than the requisite specifications or not.

If the actual specifications are less than the requisite specifications, then the console 30 does not permit the image capturing apparatus 22 to apply the radiation X in step S31. Specifically, the image capturing condition manager 98a of the console 30 sends a signal for inhibiting the radiation source 74 from applying the radiation X, to the radiation source controller 78 of the image capturing apparatus 22. The console 30 displays a message indicative of the inhibition of the application of the radiation X on its display monitor, after which control goes back to step S25. If the actual specifications are the same as or better than the requisite specifications, then control goes to step S32.

Based on the display on the console 30, the radiological technician identifies the patient 71 to be imaged first, and calls the identified patient 71 into the image capturing room. When the identified patient 71 goes into the image capturing room, the patient ID reader 28 located near the entrance/exit of the image capturing room reads the patient ID of the patient 71 from the patient tag 19 thereof, and sends the read patient ID to the console 30 in step S32.

In step S33, the patient information manager 102 of the console 30 checks the patient ID (specified patient ID) which is specified by the RIS server 14 as the patient ID of a patient 71 that is planned to be imaged, and the patient ID (actual patient ID) which is read by the patient ID reader 28 from the patient tag 19 of the patient 71 that has actually gone into the image capturing room, against each other.

If the specified patient ID and the actual patient ID do not match each other, then the console 30 does not permit the image capturing apparatus 22 to apply the radiation X in step S34. Specifically, the patient information manager 102 of the console 30 sends a signal for inhibiting the radiation source 74 from applying the radiation X, to the radiation source controller 78 of the image capturing apparatus 22. The console 30 displays a message indicative of the inhibition of the application of the radiation X on its display monitor, after which control goes back to step S32. If the specified patient ID and the actual patient ID match each other, then the console 30 permits the image capturing apparatus 22 to apply the radiation X to capture a radiation image of the patient 71.

The steps S25 through S31 and the steps S32 through S34 may be switched around, or may be carried out concurrently.

If the specified patient ID and the actual patient ID do not match each other, but if the combination of the actual patient ID and the actual cassette ID is proper, or in other words, if the order of patients to be imaged is wrong, but if the details of the image capturing request are satisfactory, then the console 30 may permit the image capturing apparatus 22 to apply the radiation X to capture a radiation image of the patient 71.

When the capturing of the radiation image is completed in step S35, the radiation image information acquired by the cassette 24 is sent to the console 30, which transmits the received radiation image information and the corresponding patient ID to the RIS server 14 in step S36. The RIS server 14 stores the received radiation image information in association with the patient ID in the patient DB 16 in step S37. The radiation image information stored in the patient DB 16 can be viewed from the image capturing request input terminal 12.

After the capturing of the radiation image is completed in step S35, the console 30 monitors whether the patient whose radiation image has been captured has left the image capturing room or not in step S38. If the patient whose radiation image has been captured has not left the image capturing room, then the console 30 does not permit the capturing of a next radiation image in step S39. For example, the console 30 sends a signal for inhibiting the radiation source 74 from applying the radiation X, to the image capturing apparatus 22. Alternatively, the console 30 displays a warning message to quickly bring the patient out of the image capturing room on its display monitor or the display device 26. If the console 30 judges in step S38 that the patient whose radiation image has been captured has left the image capturing room, then control goes to step S40.

The console 30 may determine whether or not a patient enters or leaves the image capturing room as follows: When the patient ID reader 28 reads the patient ID of a certain patient for the first time, the console 30 may judge that the patient has entered the image capturing room, and when the patient ID reader 28 reads the patient ID of the same patient twice, the console 30 may judge that the patient has left the image capturing room. Alternatively, the patient ID reader 28 may have two reading sensors, and the console 30 may determine whether or not a patient enters or leaves the image capturing room, based on the sequence in which the two reading sensors read the patient ID. Specifically, one of the two reading sensors is positioned as an inner reading sensor closer to the inside of the image capturing room and the other reading sensor is positioned an outer reading sensor closer to the outside of the image capturing room, for example. In this case, when the outer reading sensor reads the patient ID earlier than the inner reading sensor, then the console 30 may judge that the patient has entered the image capturing room, and when the inner reading sensor reads the patient ID earlier than the outer reading sensor, then the console 30 may judge that the patient has left the image capturing room.

In step S40, the console 30 monitors whether the cassette 24 which has captured the radiation image has been taken out of the image capturing room or not. If the console 30 judges that the cassette 24 which has captured the radiation image has not been taken out of the image capturing room, then the console 30 does not permit the capturing of a next radiation image in step S41, as with step S39. If the console 30 judges that the cassette 24 which has captured the radiation image has been taken out of the image capturing room, then control goes to step S42 in which the console 30 permits the capturing of a next radiation image. The console 30 may determine whether a cassette is taken out of the image capturing room or not in the same manner as with step S38.

3. Advantages of the Second Embodiment

According to the second embodiment, as described above, the requisite specifications of a cassette 24 and the actual specifications of a cassette 24 are compared with each other, and it is determined whether to permit a radiation image to be captured or not, based on the result of the cassette specifications comparison. Therefore, the cassette 24 is reliably prevented from being mistaken.

If the console 30 judges that the capturing of a radiation image is not to be permitted based on the result of the comparison of the specifications of cassettes 24 and the result of the patient ID check, then the console 30 inhibits the radiation source 74 from applying the radiation X to the patient 71. Therefore, if the console 30 judges that the capturing of a radiation image is not to be permitted, the radiation X is automatically inhibited from being applied to the patient 71 for higher safety.

If the actual specifications of the cassette 24 are the same as or better than the requisite specifications, then the console 30 permits the radiation X to be applied to the patient 71. Accordingly, even when the actual specifications are not the same as the requisite specifications, but are better than the requisite specifications, the radiation X is permitted to be applied to the patient 71. Consequently, even if actual cassettes are available in few types, radiation images can be captured in those cassettes while meeting the requisite specifications.

When the cassette 24 receives the cassette ID request signal from the cassette ID reader 27, the cassette 24 switches from the power saving mode to the normal mode. Therefore, the power consumption of the cassette 24 is reduced when it does not capture a radiation image.

The console 30 checks the specified patient ID that is input to the console 30 as the patient ID of a patient 71 which is planned to be imaged and the actual patient ID that is supplied to the console 30 as the patient ID of a patient 71 which is actually to be imaged, with each other. Therefore, the patient 71 is reliably prevented from being mistaken.

When there are a plurality of image capturing requests sent to the radiation image capturing system 20a, if the patient ID (specified patient ID) that is downloaded from the RIS server 14 to the console 30 based on the first image capturing request and the patient ID (actual patient ID) that is supplied from the patient ID reader 28 to the console 30 do not match each other, then, with respect to each of the remaining image capturing requests, the patient ID (specified patient ID) that is downloaded from the RIS server 14 to the console 30 and the patient ID (actual patient ID) that is supplied from the patient ID reader 28 to the console 30 are checked against each other. If the specified patient ID with respect to either one of the remaining image capturing requests and the actual patient ID match each other, then the console 30 determines the specifications of the cassette 24 and determines whether to permit the capturing a radiation image with respect to the remaining image capturing request representing the matching specified patient ID. Therefore, even if an error occurs in the sequence of radiation images to be captured, radiation images can quickly be captured by ignoring the sequence of radiation images to be captured.

After a radiation image of a patient 71 is captured in a cassette 24 in the image capturing room, the console 30 temporarily inhibits a radiation image of a next patient 71 from being captured until the patient ID reader 28 and the cassette ID reader 27 which are located near the entrance/exit of the image capturing room detect, respectively, when the imaged patient 71 has left the image capturing room and when the cassette 24 has been taken out of the image capturing room. Accordingly, patients 71 and cassettes 24 which are close in the image capturing sequence are prevented from being mixed up or mistaken.

C. Modifications

The present invention is not limited to the above embodiments, but various changes and modifications may be made therein, for example, as indicated by (1) through (9) shown below.

(1) Radiation image capturing systems 20, 20a:

In each of the above embodiments, the image capturing systems 20, 20a are placed in the operating room 31 or the image capturing room. However, the image capturing systems 20, 20a may be a movable system for use in visiting hospital rooms.

In each of the above embodiments, the image capturing systems 20, 20a are included in the RISs 10, 10A, respectively. However, the image capturing systems 20, 20a may be used alone. If the image capturing systems 20, 20a are used alone, cassette IDs, patient IDs, and cassette specifications may be input directly to the console 30.

In the first embodiment, both the cassette ID and the patient ID are employed. However, either the cassette ID or the patient ID may be employed. Similarly, in the second embodiment, both the cassette specifications and the patient ID are employed. However, either the cassette specifications or the patient ID may be employed.

(2) Radiation Conversion Panel (Radiation Detector 40):

In each of the above embodiments, the radiation detector 40 housed in the radiation detecting cassette 24 directly converts the dose of the applied radiation X into an electric signal with the photoelectric conversion layer 51. However, the radiation image capturing system may employ a radiation detector including a scintillator for converting the applied radiation X into visible light and a solid-state detecting device such as of amorphous silicon (a-Si) or the like for converting the visible light into an electric signal (see Japanese Patent No. 3494683).

Alternatively, the radiation image capturing system may employ a light-conversion radiation detector for acquiring radiation image information. The light-conversion radiation detector operates as follows: When a radiation is applied to a matrix of solid-state detecting devices, the solid-state detecting devices store an electrostatic latent image depending on the dose of the applied radiation. For reading the stored electrostatic latent image, reading light is applied to the solid-state detecting devices to cause the solid-state detecting devices to generate an electric current representing radiation image information. When erasing light is applied to the radiation detector, radiation image information representing a residual electrostatic latent image is erased from the radiation detector, which can thus be reused (see Japanese Laid-Open Patent Publication No. 2000-105297).

(3) Specifications of the Conversion Panel.

In the second embodiment, the sensitivity and size of the cassette 24 (radiation detector 40) are used as specifications of the cassette 24. However, the resolution of the cassette 24, the number of radiation images that can be captured by the cassette 24, and the radiation detecting method of the cassette 24 may be used as specifications of the cassette 24.

(4) Conversion Panel Identification Information (Cassette ID):

In the first embodiment, when the cassette ID supplied from the RIS server 14 to the radiation image capturing system 20 and the cassette ID read from the cassette 24 match each other, a radiation image of the patient 71 is permitted to be captured. However, if these cassette IDs are related to each other, they may not necessarily match each other. For example, it may be possible for security reasons to have a number contained in one of the cassette IDs and a number contained in the other cassette ID intentionally different from each other according to certain rules.

In the first embodiment, one cassette ID at a time is supplied from the RIS server 14 to the radiation image capturing system 20. However, the cassette IDs of a plurality of cassettes 24 which meet specifications required for capturing radiation images may be simultaneously supplied from the RIS server 14 to the radiation image capturing system 20, and if a cassette 24 having one of those supplied cassette IDs is used to capture a radiation image, then the radiation image may be permitted to be captured by the cassette 24.

(5) Database of the Conversion Panel (Cassette DB 17):

In each of the above embodiments, the cassette DB 17 stores the cassette IDs, the specifications, and the details of image capturing requests that can be handled by the cassettes 24, in association with each other. However, a database for storing the cassette IDs and the specifications of cassettes 24 in association with each other and a database for storing the details of image capturing requests and the specifications of cassettes 24 in association with each other may be employed separately from each other.

(6) Conversion Panel Identification Information Reading Unit:

In each of the above embodiments, the console 30 has a function to read the cassette ID from the cassette 24. However, such a function may be provided by another device or apparatus, such as the image capturing apparatus 22.

In the second embodiment, the cassette ID reader 27 is located near the entrance/exit of the image capturing room. However, the cassette ID reader 27 may be located anywhere insofar as it can read the cassette ID. For example, the cassette ID reader 27 may be located near the surgical table, or may be incorporated in the console 30 or the image capturing apparatus 22. The cassette ID reader 27 may read the cassette ID in a contact manner, rather than in a non-contact manner.

(7) Patient Identification Information (Patient ID):

As with the conversion panel identification information (cassette ID), the patient ID supplied from the RIS server 14 to the radiation image capturing system 20 and the patient ID read from the patient tag 19 may not match each other.

In each of the above embodiments, when the patient ID (specified patient ID) supplied from the RIS server 14 to the radiation image capturing system 20 and the patient ID (actual patient ID) read by the patient ID reader 28 match each other, a radiation image of the patient 71 is permitted to be captured. However, if these patient IDs are related to each other, they may not necessarily match each other. For example, it may be possible for security reasons to have a number contained in one of the patient IDs and a number contained in the other patient ID intentionally different from each other according to certain rules.

(8) Patient Identification Information Storing Unit (Patient Tag 19) and Patient Identification Information Reading Unit (Patient ID Reader 28):

In each of the above embodiments, the patient tag 19 is employed as a medium or means for storing the patient ID. However, any medium or means may be used to store the patient ID. For example, a band with a printed bar code which can be placed around a wrist of the patient 71 may be used as a medium for storing the patient ID. If such a band with a printed bar code is used, then a bar-code reader may be used as the patient ID reader 28.

In each of the above embodiments, the patient ID reader 28 is located near the entrance/exit of the operating room 31 or the image capturing room. However, the patient ID reader 28 may be located anywhere insofar as it can read the patient ID. For example, the patient ID reader 28 may be located in or on the surgical table or in the cassette 24.

Figure 11:
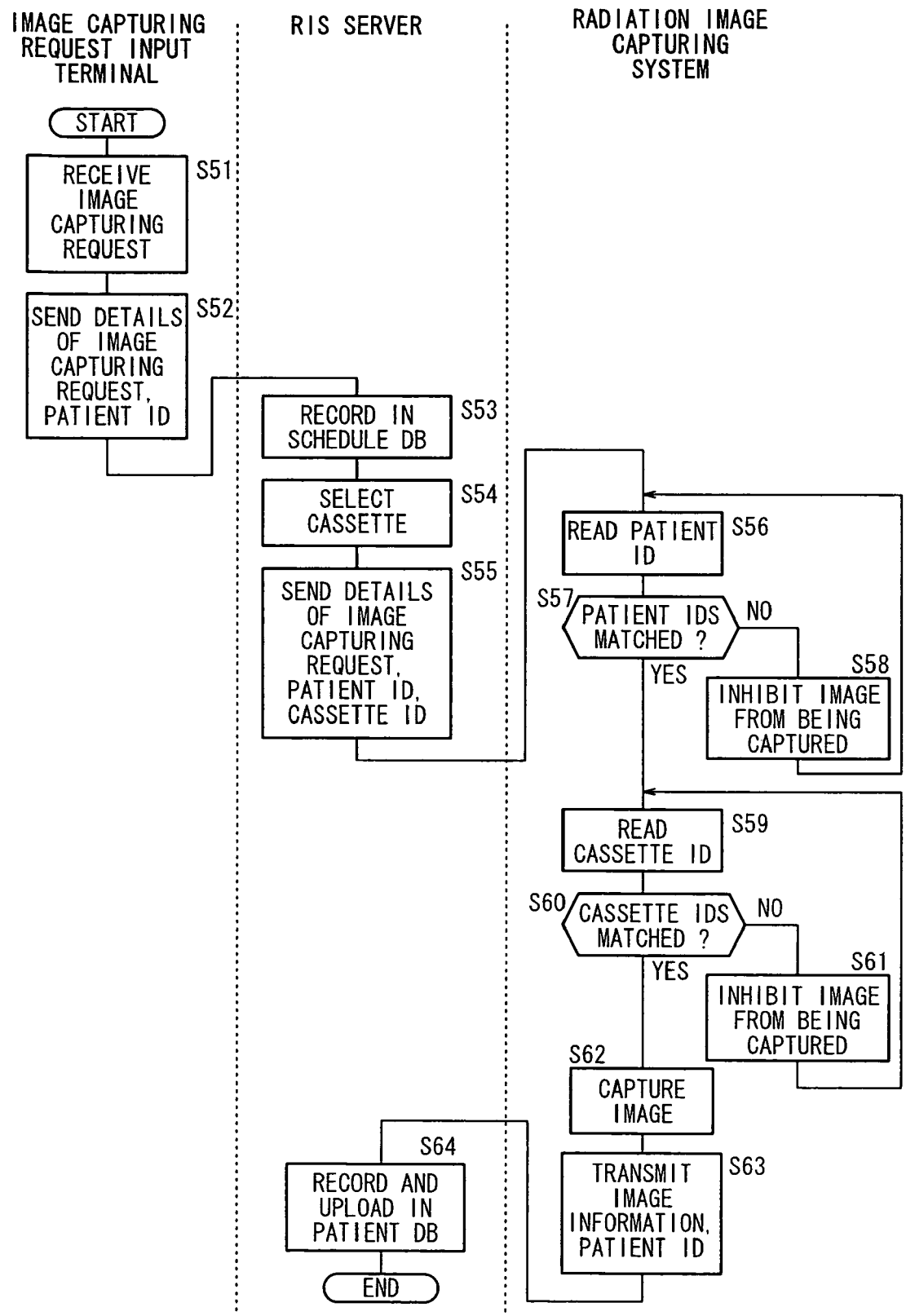
FIG. 11 is a flowchart of a modification of the operation sequence shown in FIG. 6.

(9) Others:

In the first embodiment (see FIG. 6), after the cassette ID is checked (steps S6 through S8), the patient ID is checked (steps S9 through S11). However, as shown in FIG. 11, the patient ID may be checked (steps S56 through S58) before the cassette ID is checked (steps S59 through S61), or the patient ID and the cassette ID may be checked concurrently.

Figure 12:
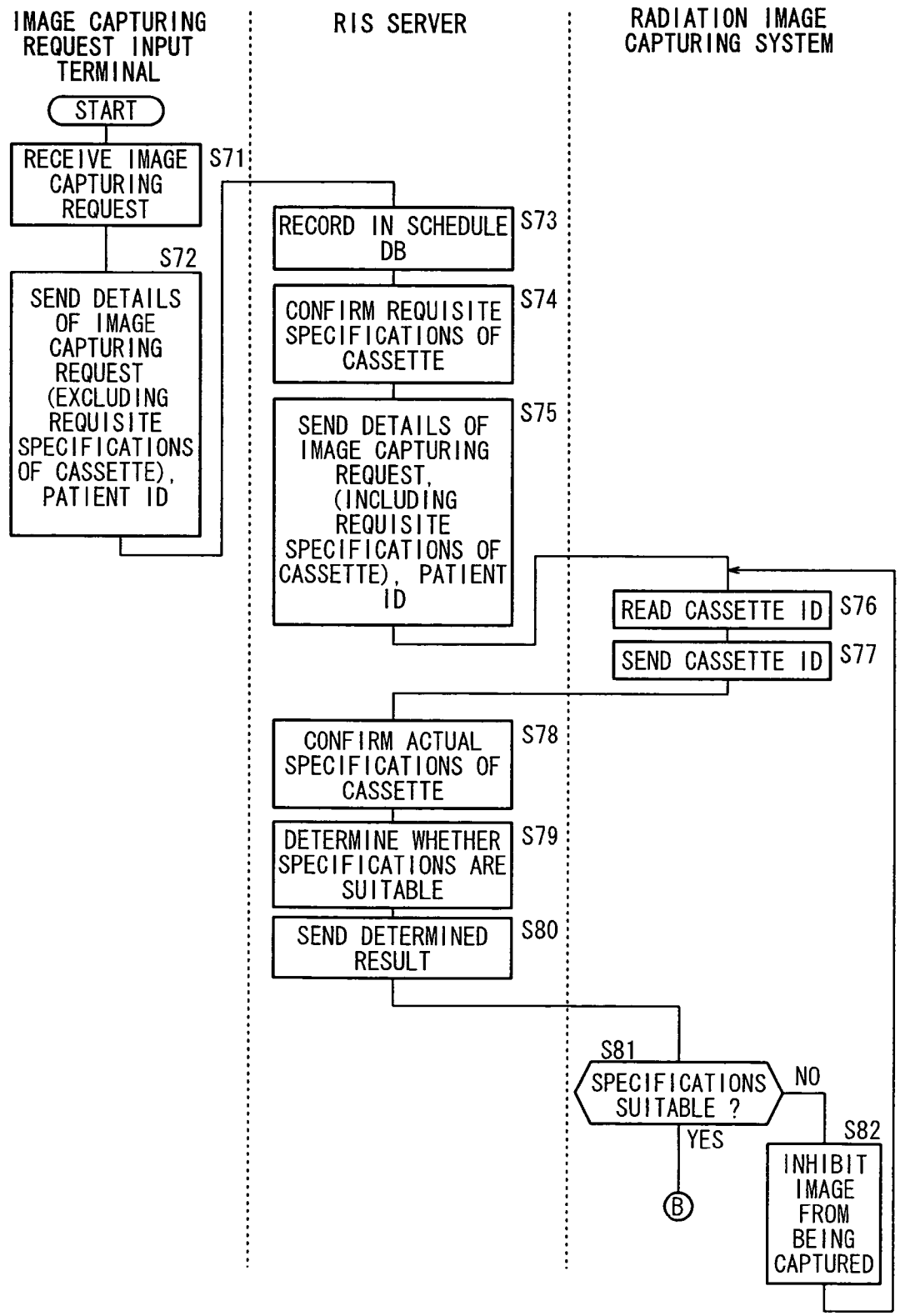
FIG. 12 is a flowchart of a part of an operation sequence according to a first modification of the operation sequence shown in FIGS. 9 and 10.

In the second embodiment (see FIG. 9), the requisite specifications of the cassette 24 are input to the image capturing request input terminal 12. However, as shown in FIG. 12, the requisite specifications of the cassette 24 may be input to the RIS server 14. Specifically, the details (an area to be imaged, etc.) of an image capturing request and the specifications (size, sensitivity, etc.) of the cassette 24 may be stored, in advance, in association with each other in the cassette DB of the RIS server 14, and the requisite specifications of the cassette 24 may not be input to the image capturing request input terminal 12, but the RIS server 14 may determine the requisite specifications of the cassette 24 based on the details of an image capturing request (step S74 shown in FIG. 12).

In the second embodiment (see FIG. 9), the radiation image capturing system 20 compares the specifications of cassettes 24 to determine whether the specifications are suitable or not (steps S29, S30). However, as shown in FIG. 12, the RIS server 14 may compare the specifications of cassettes 24 to determine whether the specifications are suitable or not. Specifically, after the RIS server 14 sends the details of the image capturing request to the image capturing system 20 in step S75 in FIG. 12, the cassette ID reader 27 reads the cassette ID in step S76, and sends the read cassette ID from the image capturing system 20 to the RIS server 14 in step S77.

The RIS server 14 reads, from the cassette DB 17, the specifications of the cassette 24 related to the cassette ID sent from the image capturing system 20, as actual specifications in step S78. Then, the RIS server 14 compares the requisite specifications of the cassette 24 confirmed in step S74 and the actual specifications confirmed in step S78 with each other to determine whether the actual specifications are suitable or not in step S79. Then, the RIS server 14 sends the determined result to the image capturing system 20 in step S80.

When the image capturing system 20 receives the determined result from the RIS server 14, the image capturing system 20 confirms the details of the determined result, i.e., whether the actual specifications are suitable or not in step S81. If the actual specifications do not meet the requisite specifications, then the image capturing system 20 does not permit a radiation image to be captured in the same manner as described above in step S82. If the actual specifications are the same as or better than the requisite specifications, then control goes to step S83 in FIG. 13.

Figure 10:
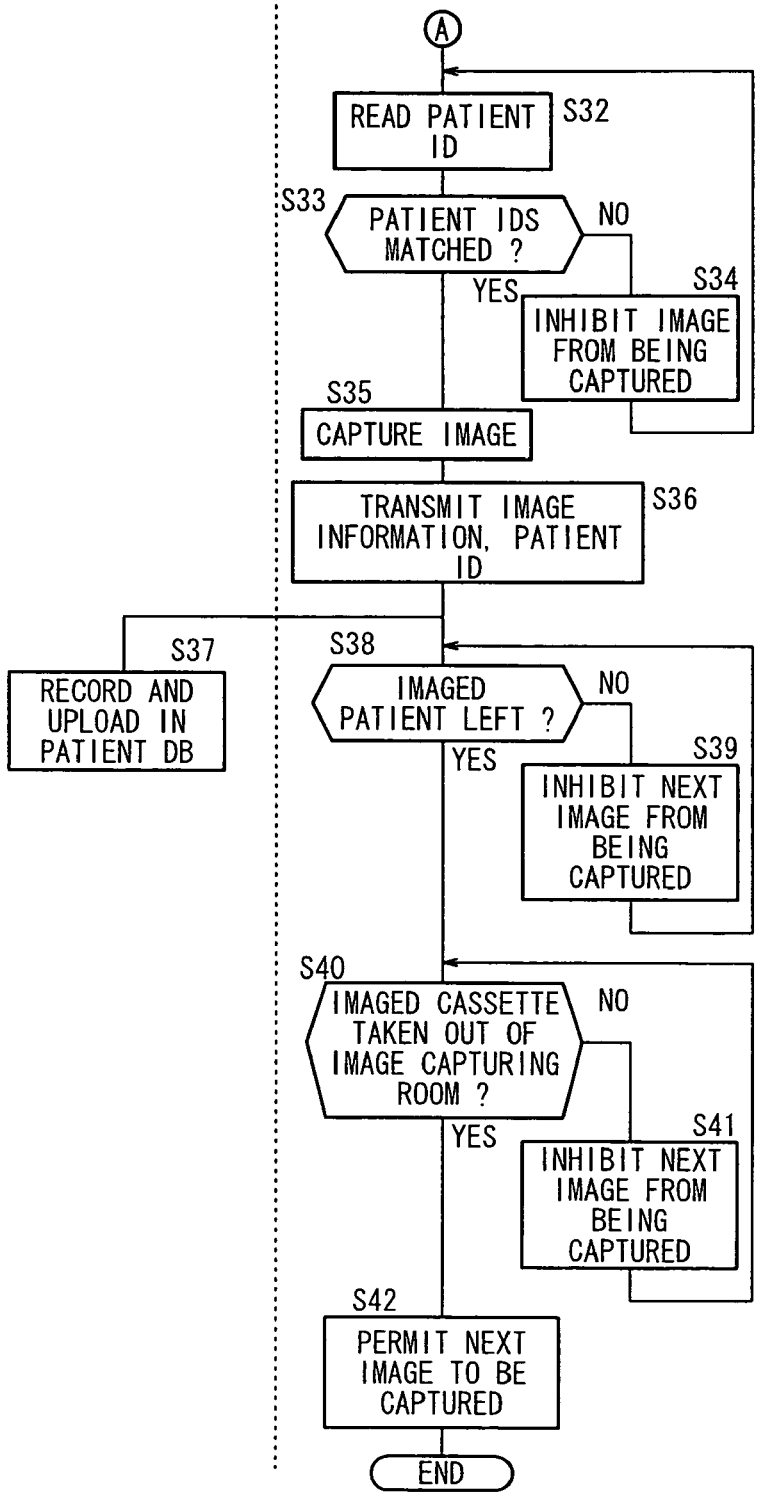
FIG. 10 is a flowchart of another part, following the part shown in FIG. 9, of the operation sequence of the radiation information system according to the second embodiment.

Steps S83 through S88 shown in FIG. 13 are the same as steps S32 through S37 shown in FIG. 10 and will not be described in detail below. In FIG. 13, steps corresponding to steps S38 through S42 shown in FIG. 10 are not included. However, those steps corresponding to steps S38 through S42 may be added to FIG. 13.

Alternatively, the cassette DB 17 of the RIS server 14 may be made accessible directly from the image capturing system 20 or the same database as the cassette DB 17 may be added to the image capturing system 20, so that the actual specifications of the cassette 24 may be confirmed by the image capturing system 20 and the actual cassette ID may not be sent to the RIS server 14 (step S26 shown in FIG. 9 is omitted and steps S27, S28 are carried out by the image capturing system 20).

Figure 14:
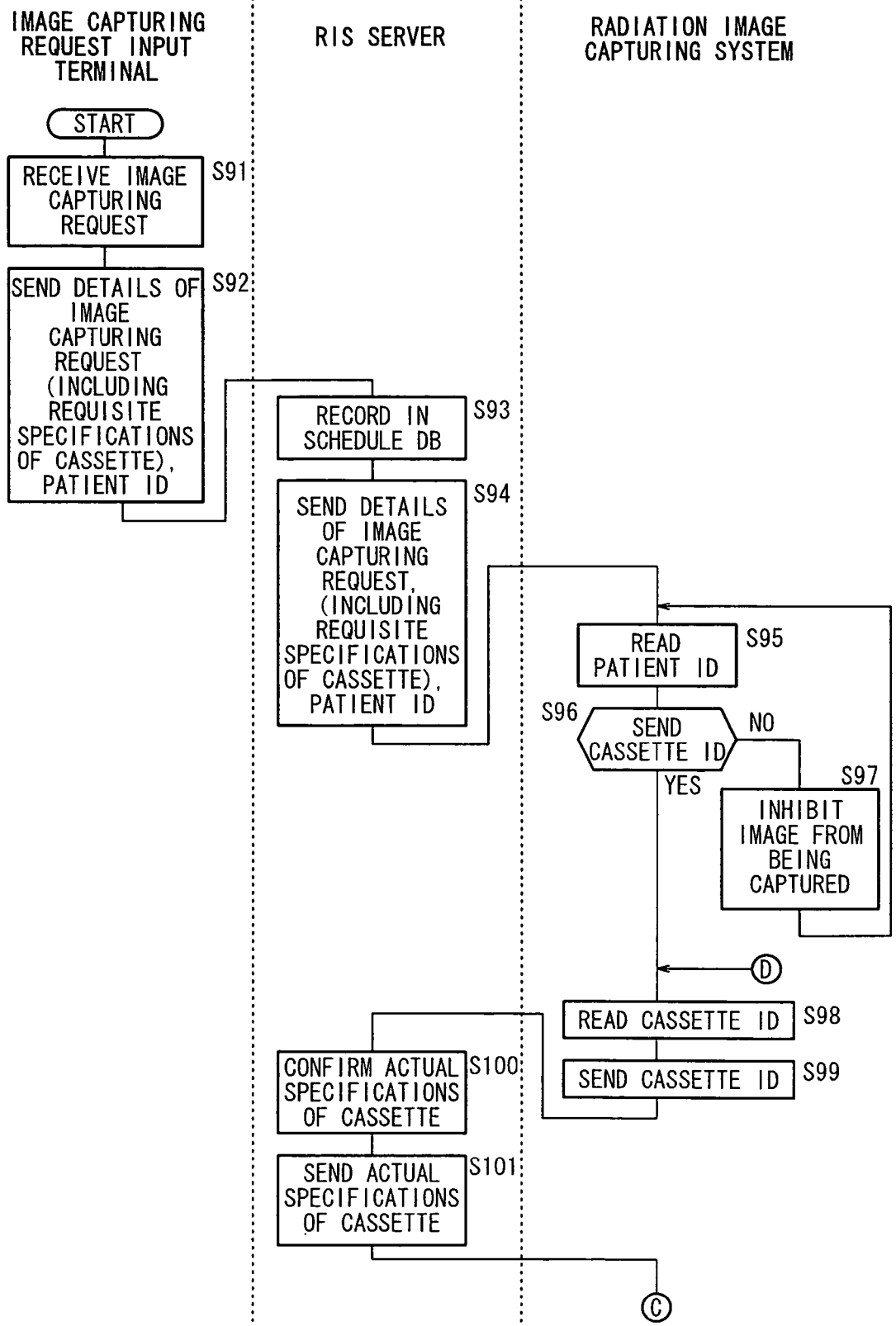
FIG. 14 is a flowchart of a part of an operation sequence according to a second modification of the operation sequence shown in FIGS. 9 and 10.
Figure 15:
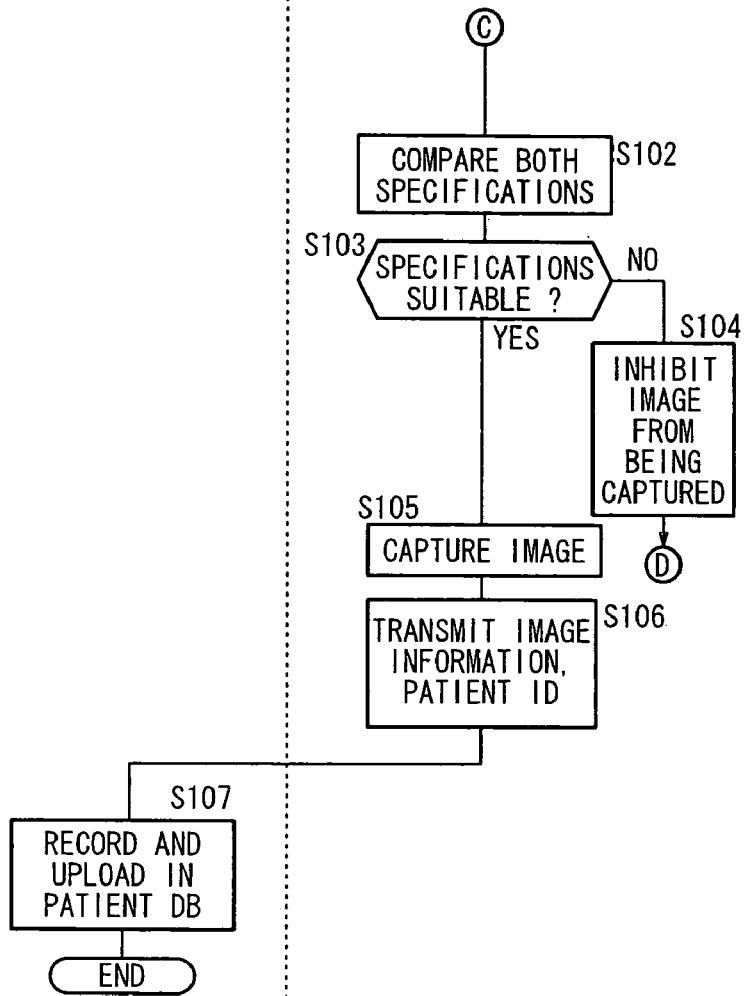
FIG. 15 is a flowchart of another part, following the part shown in FIG. 14, of the operation sequence according to the second modification.

In the second embodiments (FIGS. 9 and 10), after the specifications of the cassette 24 are determined (steps S25 through S31), the patient ID is checked (steps S32 through S34). However, as shown in FIGS. 14 and 15, the patient ID may be checked (steps S95 through S97) before the specifications of the cassette 24 are determined (steps S98 through S104), or alternatively, the patient ID may be checked and the specifications of the cassette 24 may be determined concurrently.

In each of the above embodiments, the console 30 is located in the operating room 31 or the image capturing room. However, the console 30 may be located outside of the operating room 31 or the image capturing room insofar as it can transmit and receive signals to and from the image capturing apparatus 22, the radiation detecting cassette 24, the display device 26, the cassette ID reader 27, and the patient ID reader 28 by way of wireless communications.

Figure 16:
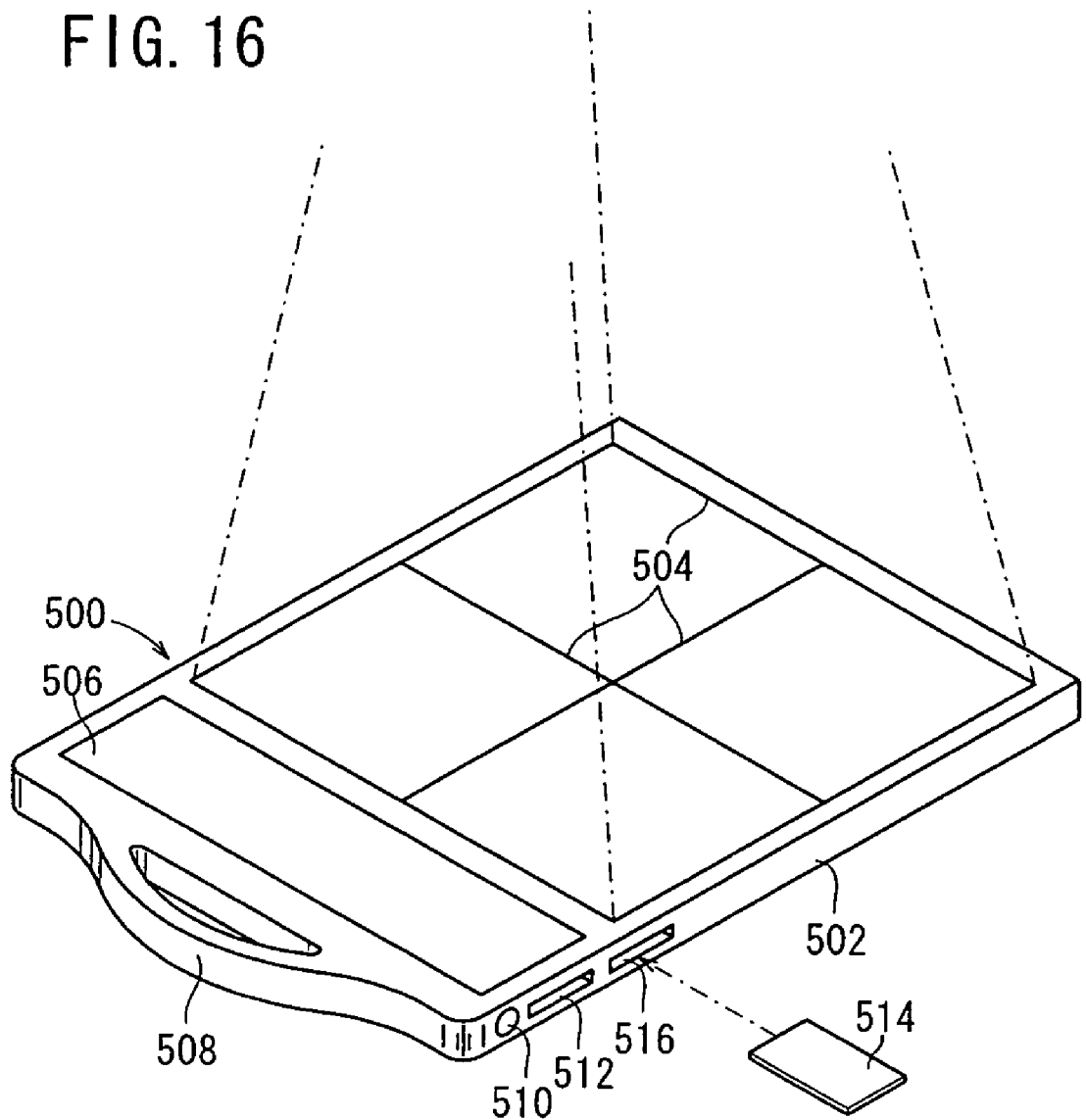
FIG. 16 is a perspective view showing a radiation detecting cassette in the radiation image capturing system according to another embodiment of the present invention.

Preferably, the radiation detecting cassette 500 (hereinafter referred to as "cassette 500") may be constructed as shown in FIG. 16.

Specifically, the cassette 500 includes a guiding line 504 drawn on the radiation-irradiated surface of a casing 502, the guiding line 504 serving as a reference for setting a captured area and a captured position. Using the guiding line 504, a subject (patient 71) can be positioned with respect to the cassette 500, and an area irradiated with the radiation X can be set, thereby recording radiation image information on an appropriate captured area.

The cassette 500 is provided with a display section 506 on an area thereof other than the captured area, for displaying various information about the cassette 500. The information which is displayed on the display section 506, includes ID information of a patient 71 whose radiation image information is to be recorded on the cassette 500, the number of times the cassette 500 has been used, an accumulated exposed radiation dose, a charging state (remaining battery level) of a battery 44 in the cassette 500, image capturing conditions of radiation image information, and a positioning image of the patient 71 with respect to the cassette 500. In this case, a technician confirms a patient 71 based on the ID information displayed on the display section 506, for example, and also previously confirms that the cassette 500 is placed in a usable state. Then, the technician positions a desired captured area of the patient 71 with respect to the cassette 500 based on the displayed positioning image, thereby capturing appropriate radiation image information.

Also, the cassette 500 is provided with a handgrip 508, whereby it is easier to handle and carry the cassette 500.

Preferably, the cassette 500 may have, on a side thereof, an input terminal 510 for an AC adapter, a USB (Universal Serial Bus) terminal 512, and a card slot 516 for inserting a memory card 514.

When the charging function of the battery 44 in the cassette 500 becomes deteriorated, or when there is not enough time to fully charge the battery 44, the input terminal 510 is connected to the AC adapter to externally supply the cassette 500 with electric power, thereby enabling the cassette 500 to be used immediately.

The USB terminal 512 or the card slot 516 may be used when the cassette 500 cannot transmit and receive information to and from external devices such as the console 30 via wireless communication. Specifically, by connecting a cable to the USB terminal 512, the cassette 500 can transmit and receive information to and from the external devices via wire communication. Alternatively, the memory card 514 is inserted into the card slot 516, and necessary information is recorded on the memory card 514. After that, the memory card 514 is removed from the card slot 516, and the memory card 514 is inserted into the external device, thereby enabling information to be transferred.

Figure 17:
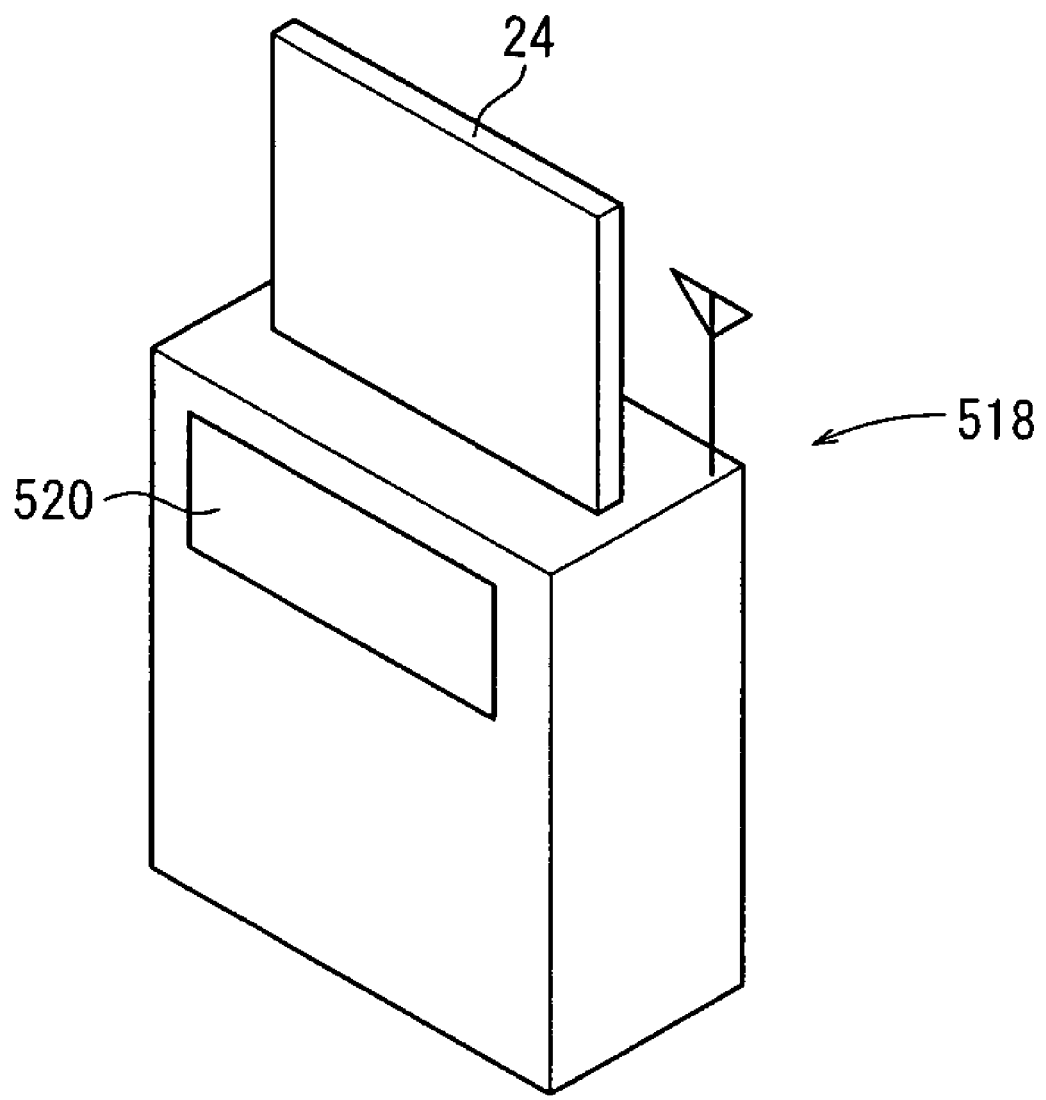
FIG. 17 is a perspective view showing a cradle which charges the radiation detecting cassette.

Preferably, a cradle 518 may be disposed in the operating room 31 or at a desired place in the hospital, into which the cassette 24 is inserted to charge the internal battery 44, as shown in FIG. 17. In this case, in addition to charging the battery 44, the cradle 518 may transmit and receive necessary information to and from external devices such as a RIS server 14, a HIS server 15, the console 30, etc. by way of wireless or wire communications of the cradle 518. The information may include radiation image information which is recorded on the cassette 24 inserted into the cradle 518.

Also, the cradle 518 may be provided with a display section 520. The display section 520 may display necessary information including a charging state of the inserted cassette 24 and radiation image information acquired from the cassette 24.

Further, a plurality of cradles 518 may be connected to a network. In this case, information about charging states of cassettes 24 inserted in respective cradles 518 can be collected through the network, and the cassette 24 in a usable state can be located.

Although certain preferred embodiments of the present invention have been shown and described in detail, it should be understood that various changes and modifications may be made therein without departing from the scope of the appended claims.

What is claimed is:

1. A method of capturing a radiation image with a radiation image capturing system including a conversion panel for detecting a radiation that has passed through a subject and converting the detected radiation into radiation image information, a conversion panel identification information reading unit for reading conversion panel identification information which is stored in the conversion panel to identify the conversion panel, from said conversion panel, and an identifying unit for identifying said conversion panel with the conversion panel identification information, said method comprising:

the image capturing permission determining step of checking, with said identifying unit, specified conversion panel identification information, which is the conversion panel identification information of a conversion panel that is planned to be used to capture a radiation image, and actual conversion panel identification information, which is the conversion panel identification information of a conversion panel that is to be actually used to capture a radiation image, against each other, and determining, with said identifying unit, whether said radiation image is permitted to be captured or not, based on the result of checking the specified and actual conversion panel identification information, wherein said radiation image capturing system further includes a patient identification information storing unit for storing patient identification information for identifying individual patients, said patient identification information storing unit being carried by the individual patients, and a patient identification information reading unit for reading the patient identification information from said patient identification information storing unit, said method further comprising:

the second image capturing permission determining step of checking, with said identifying unit, specified patient identification information, which is the patient identification information of a patient that is planned to be imaged, and actual patient identification information, which is the patient identification information of a patient that is to be actually imaged and which is read from said patient identification information storing unit by said patient identification information reading unit, against each other, and determining, with said identifying unit, whether said radiation image is permitted to be captured or not, based on the result of checking the specified and actual patient identification information.

2. A method according to claim 1, further comprising the steps of:

emitting a request signal for requesting said actual conversion panel identification information, from said conversion panel identification information reading unit into a predetermined range for a predetermined time period until communications with the conversion panel that is to be actually used are established; and sending said actual conversion panel identification information from the conversion panel that is to be actually used, to said conversion panel identification information reading unit when the conversion panel that is to be actually used receives said request signal.

3. A method according to claim 1, further comprising the step of inhibiting a radiation source from applying said radiation if said identifying unit judges that said radiation image is not permitted to be captured in said image capturing permission determining step.

4. A method according to claim 1, wherein said radiation image capturing system further includes an image capturing request input terminal for inputting an image capturing request for the radiation image in association with said patient identification information, and a server having a conversion panel attribute information database for storing said conversion panel identification information and specification information of said conversion panel in association with each other as conversion panel attribute information, said method further comprising the steps of:

receiving said image capturing request in association with said patient identification information at said image capturing request input terminal;

sending details of said image capturing request and said patient identification information from said image capturing request input terminal to said server;

selecting, with said server, a conversion panel corresponding to the details of said image capturing request using said conversion panel attribute information database; and sending conversion panel identification information of the selected conversion panel, together with the details of the image capturing request and the patient identification information of the patient associated with said image capturing request, from said server to said identifying unit.

5. A radiation image capturing system for carrying out a method according to claim 1.

6. A radiation information system comprising a radiation image capturing system, a server, and an image capturing request input terminal for carrying out a method according to claim 4.

7. A method of capturing a radiation image with a radiation image capturing system including a conversion panel for detecting a radiation that has passed through a subject and converting the detected radiation into radiation image information, a conversion panel identification information reading unit for reading conversion panel identification information which is stored in the conversion panel to identify the conversion panel, from said conversion panel, and an identifying unit for identifying said conversion panel with the conversion panel identification information, said method comprising:

the specification matching determining step of comparing, with said identifying unit, requisite specifications, which are specifications of a conversion panel that is planned to be used to capture a radiation image, and actual specifications, which are specifications of a conversion panel that is to be actually used to capture a radiation image and from which the conversion panel identification information is read by said conversion panel identification information reading unit, with each other, and determining whether said actual specifications match said requisite specifications or not; and the image capturing permission determining step of determining, with said identifying unit, whether said radiation image is permitted to be captured or not, based on the result in the specification matching determining step, wherein said radiation image capturing system further includes a patient identification information storing unit for storing patient identification information for identifying individual patients, said patient identification information storing unit being carried by the individual patients, and a patient identification information reading unit for reading the patient identification information from said patient identification information storing unit, said method further comprising:

the second image capturing permission determining step of checking, with said identifying unit, specified patient identification information, which is the patient identification information of a patient that is planned to be imaged, and actual patient identification information, which is the patient identification information of a patient that is to be actually imaged and which is read from said patient identification information storing unit by said patient identification information reading unit, against each other, and determining, with said identifying unit, whether said radiation image is permitted to be captured or not, based on the result of checking the specified and actual patient identification information.

8. A method according to claim 7, wherein the specifications of the conversion panel represent a sensitivity or size of the conversion panel.

9. A method according to claim 7, further comprising the step of inhibiting a radiation source from applying said radiation if said identifying unit judges that said radiation image is not permitted to be captured in said image capturing permission determining step.

10. A method according to claim 7, further comprising the step of permitting a radiation source to apply said radiation if said identifying unit judges that said actual specifications are the same as or better than said requisite specifications in said image capturing permission determining step.

11. A method according to claim 7, further comprising the step of bringing said conversion panel that is to be actually used, from a power saving mode to a normal mode when said conversion panel identification information reading unit requests the conversion panel to send said conversion panel identification information therefrom.

12. A method according to claim 7, wherein a plurality of image capturing requests are sent to said radiation image capturing system, further comprising the step of, if said specified patient identification information and said actual patient identification information do not match each other with respect to a first one of said image capturing requests, carrying out said second image capturing permission determining step again with respect to the remaining ones of the image capturing requests.

13. A method according to claim 7, wherein said patient identification information reading unit and said conversion panel identification information reading unit are disposed near an exit of a place in which said radiation image is captured, further comprising the steps of:

reading, with said patient identification information reading unit, the patient identification information of a patient whose radiation image has been captured, and sending the read patient identification information to said identifying unit;

reading, with said conversion panel identification information reading unit, the conversion panel identification information of a conversion panel which has captured a radiation image, and sending the read conversion panel identification information to said identifying unit; and temporarily inhibiting, with said identifying unit, a next radiation image from being captured until the patient identification information of the patient whose radiation image has been captured and the conversion panel identification information of the conversion panel which has captured the radiation image are received by said identifying unit.

14. A method according to claim 7, wherein said radiation image capturing system further includes an image capturing request input terminal for inputting an image capturing request for the radiation image in association with said patient identification information, and a server having a conversion panel identification information database for storing said conversion panel identification information in association with specifications of said conversion panel and an image capturing request detail database for storing details of the image capturing request in association with the specifications of said conversion panel, said method further comprising the steps of:

receiving, with said image capturing request input terminal, the image capturing request in association with the patient identification information;

sending details of the image capturing request and said patient identification information from said image capturing request input terminal to said server;

confirming, with said server, the requisite specifications which are specifications of a conversion panel corresponding to the details of the image capturing request, using said image capturing request detail database;

sending the confirmed requisite specifications, together with the details of the image capturing request and the patient identification information associated with said image capturing request, from said server to said identifying unit;

sending the conversion panel identification information read by said conversion panel identification information reading unit, from said identifying unit to said server;

confirming, with said server, actual specifications which are specifications of a conversion panel corresponding to the conversion panel identification information sent from said identifying unit, using said conversion panel identification information database;

sending the confirmed actual specifications from said server to said identifying unit;

comparing, with said identifying unit, the sent actual specifications and the sent requisite specifications with each other, and determining whether the actual specifications match said requisite specifications or not; and determining, with said identifying unit, whether said radiation image is permitted to be captured or not, based on the result of the step of determining whether the actual specifications match said requisite specifications or not.

15. A method according to claim 7, wherein said radiation image capturing system further includes an image capturing request input terminal for inputting an image capturing request for the radiation image in association with said patient identification information, and a server having a conversion panel identification information database for storing said conversion panel identification information in association with specifications of said conversion panel and an image capturing request detail database for storing details of the image capturing request in association with the specifications of said conversion panel, said method further comprising the steps of:

receiving, with said image capturing request input terminal, the image capturing request in association with the patient identification information;

sending details of the image capturing request and said patient identification information from said image capturing request input terminal to said server;

confirming, with said server, the requisite specifications which are specifications of a conversion panel corresponding to the details of the image capturing request, using said image capturing request detail database;

sending the confirmed requisite specifications, together with the details of the image capturing request and the patient identification information associated with said image capturing request, from said server to said identifying unit;

sending the conversion panel identification information read by said conversion panel identification information reading unit, from said identifying unit to said server;

confirming, with said server, the actual specifications which are specifications of a conversion panel corresponding to the conversion panel identification information sent from said identifying unit, using said conversion panel identification information database;

comparing, with said server, the confirmed actual specifications and the confirmed requisite specifications with each other, and determining whether the actual specifications match said requisite specifications or not;

sending the result of the step of determining whether the actual specifications match said requisite specifications or not, from said server to said identifying unit; and determining, with said identifying unit, whether said radiation image is permitted to be captured or not, based on the sent result in the step of sending the result of the step of determining whether the actual specifications match said requisite specifications or not.

16. A radiation image capturing system for carrying out a method according to claim 7.

17. A radiation information system comprising a radiation image capturing system, a server, and an image capturing request input terminal for carrying out a method according to claim 14.

18. A radiation information system comprising a radiation image capturing system, a server, and an image capturing request input terminal for carrying out a method according to claim 15.

* * * * *